(12) United States Patent
Hughes et al.

(10) Patent No.: US 7,831,290 B2
(45) Date of Patent: Nov. 9, 2010

(54) MRI BIOPSY DEVICE LOCALIZATION FIXTURE

(75) Inventors: Robert J. Hughes, Cincinnati, OH (US); Timothy G. Dietz, Terrace Park, OH (US); Michael J. Andreyko, Cincinnati, OH (US); Kent Swendseid, Seattle, WA (US); Jay Wilkins, Bozeman, MT (US); William E. Clem, Bozeman, MT (US)

(73) Assignee: Devicor Medical Products, Inc., Cincinnati, OH (US)

( * ) Notice: Subject to any disclaimer, the term of this patent is extended or adjusted under 35 U.S.C. 154(b) by 1186 days.

(21) Appl. No.: 11/103,959

(22) Filed: Apr. 12, 2005

(65) Prior Publication Data

US 2005/0283069 A1     Dec. 22, 2005

Related U.S. Application Data

(60) Provisional application No. 60/573,510, filed on May 21, 2004.

(51) Int. Cl.
*A61B 5/05* (2006.01)
*A61B 17/32* (2006.01)

(52) U.S. Cl. .............. 600/411; 600/415; 600/417; 600/427; 606/167

(58) Field of Classification Search .............. 600/417, 600/427, 564, 411, 415, 429; 606/130, 131, 606/167; 378/37, 208
See application file for complete search history.

(56) References Cited

U.S. PATENT DOCUMENTS

| 875,745 | A |  | 12/1907 | Hanes |
|---|---|---|---|---|
| 4,169,060 | A |  | 9/1979 | Columbus |
| 4,875,478 | A | * | 10/1989 | Chen .......................... 600/429 |
| 5,057,085 | A |  | 10/1991 | Kopans |
| 5,195,985 | A |  | 3/1993 | Hall |
| 5,211,165 | A |  | 5/1993 | Dumoulin et al. |
| 5,307,808 | A |  | 5/1994 | Dumoulin et al. |

(Continued)

FOREIGN PATENT DOCUMENTS

DE          92 06 853.7          10/1992

(Continued)

OTHER PUBLICATIONS

Noras Medizintechnik, Operator Manual, Model MR-B1 160, Revision 3, pp. 1-11.

(Continued)

*Primary Examiner*—Eric F Winakur
*Assistant Examiner*—Katherine L Fernandez
(74) *Attorney, Agent, or Firm*—Frost Brown Todd LLC

(57) ABSTRACT

A localization mechanism, or fixture, is used in conjunction with a breast coil for breast compression and for guiding a core biopsy instrument during prone biopsy procedures in both open and closed Magnetic Resonance Imaging (MRI) machines. The localization fixture includes a three-dimensional Cartesian positionable guide for supporting and orienting an MRI-compatible biopsy instrument, and, in particular, a sleeve to a biopsy site of suspicious tissues or lesions. A z-stop enhances accurate insertion, prevents over-insertion or inadvertent retraction of the sleeve. The sleeve receives a probe of the MRI-compatible biopsy instrument and may contain various features to enhance its imagability, to enhance vacuum and pressure assist therethrough, etc.

32 Claims, 33 Drawing Sheets

U.S. PATENT DOCUMENTS

| | | | |
|---|---|---|---|
| 5,318,025 A | 6/1994 | Dumoulin et al. | |
| 5,437,277 A | 8/1995 | Dumoulin et al. | |
| 5,443,066 A | 8/1995 | Dumoulin et al. | |
| 5,445,150 A | 8/1995 | Dumoulin et al. | |
| 5,458,112 A | 10/1995 | Weaver | |
| 5,514,131 A | 5/1996 | Edwards | |
| 5,526,822 A | 6/1996 | Burbank et al. | |
| 5,531,703 A | 7/1996 | Skwarek et al. | |
| 5,541,972 A | 7/1996 | Anthony | |
| 5,560,373 A | 10/1996 | De Santis | |
| 5,611,352 A * | 3/1997 | Kobren et al. | 600/564 |
| 5,678,549 A | 10/1997 | Heywang-Koebrunner et al. | |
| 5,715,822 A | 2/1998 | Watkins et al. | |
| 5,775,333 A | 7/1998 | Burbank et al. | |
| 5,782,764 A | 7/1998 | Werne | |
| 5,800,389 A | 9/1998 | Burney et al. | |
| 5,827,305 A * | 10/1998 | Gordon | 606/159 |
| 5,830,219 A | 11/1998 | Bird et al. | |
| 5,855,554 A | 1/1999 | Schneider et al. | |
| 5,882,305 A | 3/1999 | Dumoulin et al. | |
| 5,913,863 A * | 6/1999 | Fischer et al. | 606/130 |
| 5,921,943 A | 7/1999 | Kass | |
| 5,954,670 A | 9/1999 | Baker | |
| 6,022,325 A | 2/2000 | Siczek et al. | |
| 6,036,632 A | 3/2000 | Whitmore, III et al. | |
| 6,048,321 A | 4/2000 | McPherson et al. | |
| 6,077,230 A | 6/2000 | Gregoire et al. | |
| 6,086,544 A * | 7/2000 | Hibner et al. | 600/568 |
| 6,142,955 A | 11/2000 | Farascioni et al. | |
| 6,165,137 A | 12/2000 | Milliman et al. | |
| 6,174,291 B1 | 1/2001 | McMahon et al. | |
| 6,203,524 B1 | 3/2001 | Burney et al. | |
| 6,261,241 B1 | 7/2001 | Burbank et al. | |
| 6,261,243 B1 | 7/2001 | Burney et al. | |
| 6,264,670 B1 | 7/2001 | Chin | |
| 6,270,506 B1 | 8/2001 | Sittek et al. | |
| 6,272,372 B1 | 8/2001 | Fisher | |
| 6,289,233 B1 | 9/2001 | Dumoulin et al. | |
| 6,321,613 B1 | 11/2001 | Avidor | |
| 6,416,510 B1 * | 7/2002 | Altman et al. | 606/41 |
| 6,428,498 B2 | 8/2002 | Uflacker | |
| 6,432,045 B2 * | 8/2002 | Lemperle et al. | 600/135 |
| 6,432,064 B1 | 8/2002 | Hibner et al. | |
| 6,447,477 B2 | 9/2002 | Burney et al. | |
| 6,471,700 B1 | 10/2002 | Burbank et al. | |
| 6,558,337 B2 * | 5/2003 | Dvorak et al. | 600/564 |
| 6,626,849 B2 | 9/2003 | Huitema et al. | |
| 6,638,235 B2 | 10/2003 | Miller et al. | |
| 6,659,338 B1 * | 12/2003 | Dittmann et al. | 235/375 |
| 6,675,037 B1 | 1/2004 | Tsekos | |
| 6,752,768 B2 | 6/2004 | Burdorff et al. | |
| 6,758,824 B1 | 7/2004 | Miller et al. | |
| 6,758,848 B2 | 7/2004 | Burbank et al. | |
| 6,770,063 B2 * | 8/2004 | Goldberg et al. | 604/326 |
| 6,846,320 B2 | 1/2005 | Ashby et al. | |
| 6,863,676 B2 | 3/2005 | Lee et al. | |
| 6,889,073 B2 | 5/2005 | Lampman et al. | |
| 6,921,943 B2 | 7/2005 | Kenney et al. | |
| 6,975,701 B2 | 12/2005 | Galkin | |
| 6,999,553 B2 | 2/2006 | Livingston | |
| 7,160,292 B2 | 1/2007 | Moorman et al. | |
| 7,171,256 B1 * | 1/2007 | Graessle et al. | 600/427 |
| 7,276,032 B2 | 10/2007 | Hibner | |
| 7,347,829 B2 | 3/2008 | Mark et al. | |
| 7,351,228 B2 | 4/2008 | Keane et al. | |
| 7,470,237 B2 | 12/2008 | Beckman et al. | |
| 2001/0049502 A1 | 12/2001 | Chen | |
| 2003/0004529 A1 | 1/2003 | Tsonton et al. | |
| 2003/0023239 A1 | 1/2003 | Burbank et al. | |
| 2003/0109802 A1 | 6/2003 | Laseke | |
| 2003/0109803 A1 | 6/2003 | Huitema et al. | |
| 2003/0199753 A1 | 10/2003 | Hibner et al. | |
| 2003/0199754 A1 | 10/2003 | Hibner et al. | |
| 2003/0199785 A1 | 10/2003 | Hibner et al. | |
| 2004/0006347 A1 | 1/2004 | Sproul | |
| 2004/0077938 A1 | 4/2004 | Mark et al. | |
| 2004/0077972 A1 * | 4/2004 | Tsonton et al. | 600/564 |
| 2004/0210161 A1 | 10/2004 | Burdorff | |
| 2004/0230157 A1 | 11/2004 | Perry et al. | |
| 2008/0161720 A1 | 7/2008 | Nicoson et al. | |
| 2008/0200834 A1 | 8/2008 | Mark et al. | |

FOREIGN PATENT DOCUMENTS

| | | |
|---|---|---|
| DE | 42 16 694 | 12/1992 |
| EP | 0 995 400 | 4/2000 |
| EP | 1 410 764 | 4/2004 |
| EP | 1598006 | 11/2005 |
| EP | 1598015 | 11/2005 |
| FR | 2 332 743 | 6/1977 |
| WO | WO 93/17620 | 9/1993 |
| WO | WO 96/14023 | 5/1996 |
| WO | WO 98/22022 | 5/1998 |
| WO | WO 02/13709 | 2/2002 |
| WO | WO 03/026509 | 4/2003 |
| WO | WO 2005/017775 | 2/2005 |

OTHER PUBLICATIONS

EPO Search Report, Application No. 07250438.4, May 21, 2007, pp. 1-5.
European Search Report, dated Jan. 5, 2004 for EPO Application No. 03252518.0.
European Search Report for EP 05 254 3171, Sep. 23, 2005, pp. 1-5.
International Search Report for PCT/US2005/017775, May 21, 2004, pp. 1-4.
European Search Report dated Sep. 25, 2007 for Application No. 07252089.3.
U.S. Appl. No. 60/573,510, filed May 21, 2004, Hughes et al.
U.S. Appl. No. 11/025,556, filed Dec. 29, 2004, Hibner et al.
U.S. Appl. No. 11/076,612, filed Mar. 10, 2005, Hughes et al.
U.S. Appl. No. 11/103,718, filed Apr. 12 2005, Tsonton et al.
U.S. Appl. No. 11/103,959, filed Apr. 12, 2005, Hughes et al.
European Search Report dated Sep. 14, 2005 for Application No. EP 05253171.
European Search Report dated Sep. 20, 2005 for Application No. PCT/US2005/017775.
Office Action dated Jul. 1, 2008 for U.S. Appl. No. 11/463,346.
Office Action dated Jul. 3, 2008 for U.S. Appl. No. 11/076,612.
Office Action dated Mar. 21, 2008 for U.S. Appl. No. 11/103,718.
Office Action dated May 23, 2008 for Chinese Application No. 200510074636.1.
Heywang Köbrunner et al., "MR-guided percutaneous excisional and incisional biopsy of breast lesions," Eur. Radiol., vol. 9 (1999) pp. 1656-1665.
Savitz, M.H., "CT-Guided Needle Procedures for Brain Lesion: 20 Years' Experience," The Mount Sinai Journal of Medicine, vo. 67(4) (Sep. 2000) pp. 318-321.
Savitz, M.H., "Free-hand CT-guided Needle for Biopsy and Drainage of Intracerebral Lesions. Ten Years Experience," Int. Surg., vol. 77 (1992) pp. 211-215.
Preliminary Patentability Report dated Nov. 21, 2006 for Application No. PCT/US2005/017775.
Written Opinion dated Sep. 29, 2005 for Application No. PCT/US2005/017775.
Daniel, B.L. et al., "An MRI-Compatible Semiautomated Vacuum-Assisted Breast Biopsy System: Initial Feasibility Study," J. of Magnetic Resonance Imaging, vol. 21 (2005) pp. 637-644.

Kuhl, C.K. et al., "Interventional Breast MR Imaging: Clinical Use of a Stereotactic Localization and Biopsy Device," Radiology, vol. 204 (1997) pp. 667-675.

Perlot, C. et al., "Multicenter study for the evaluation of a dedicated biopsy device for MR-guided vacuum biopsy of the breast," Eur. Radiol., vol. 12 (2002) pp. 1463-1470.

Viehweg, P. et al., "MR-guided interventional breast procedures considering vacuum biopsy in particular," Eur. J. of Radiol., vol. 42 (2002) pp. 32-39.

EnCor™ *MRI* Specifications and Breast Biopsy System, SenoRx, 2005, pp. 1-2.

* cited by examiner

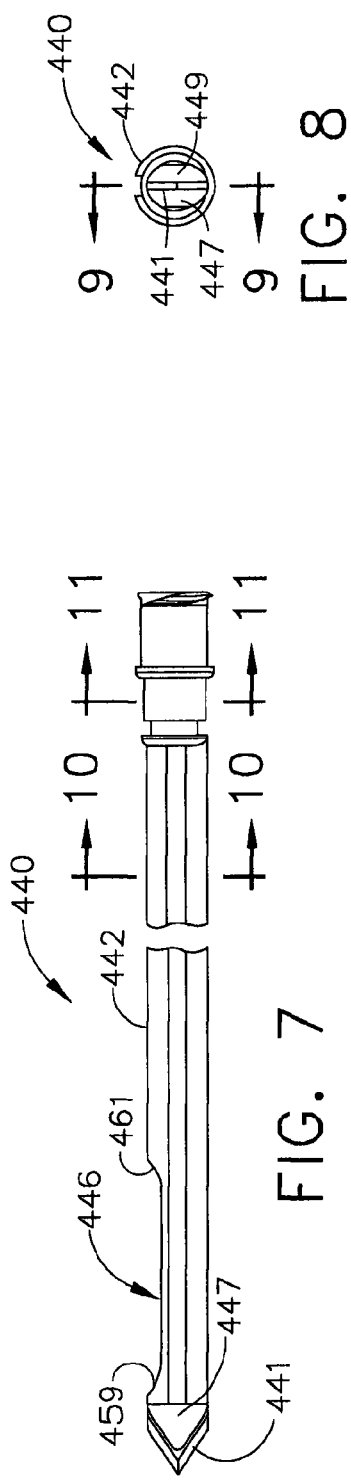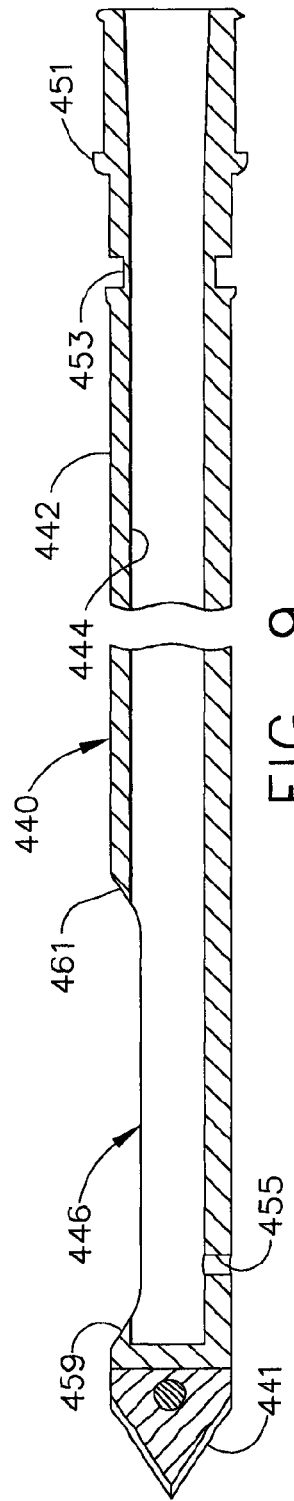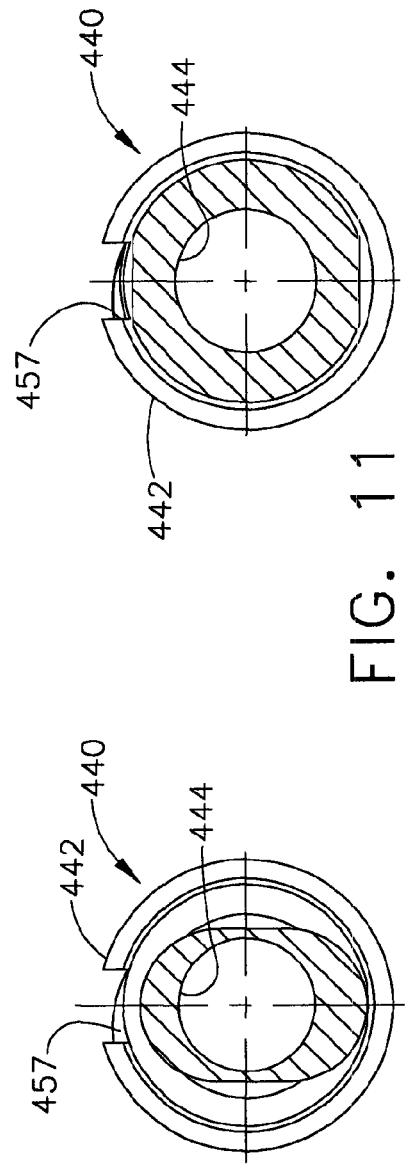

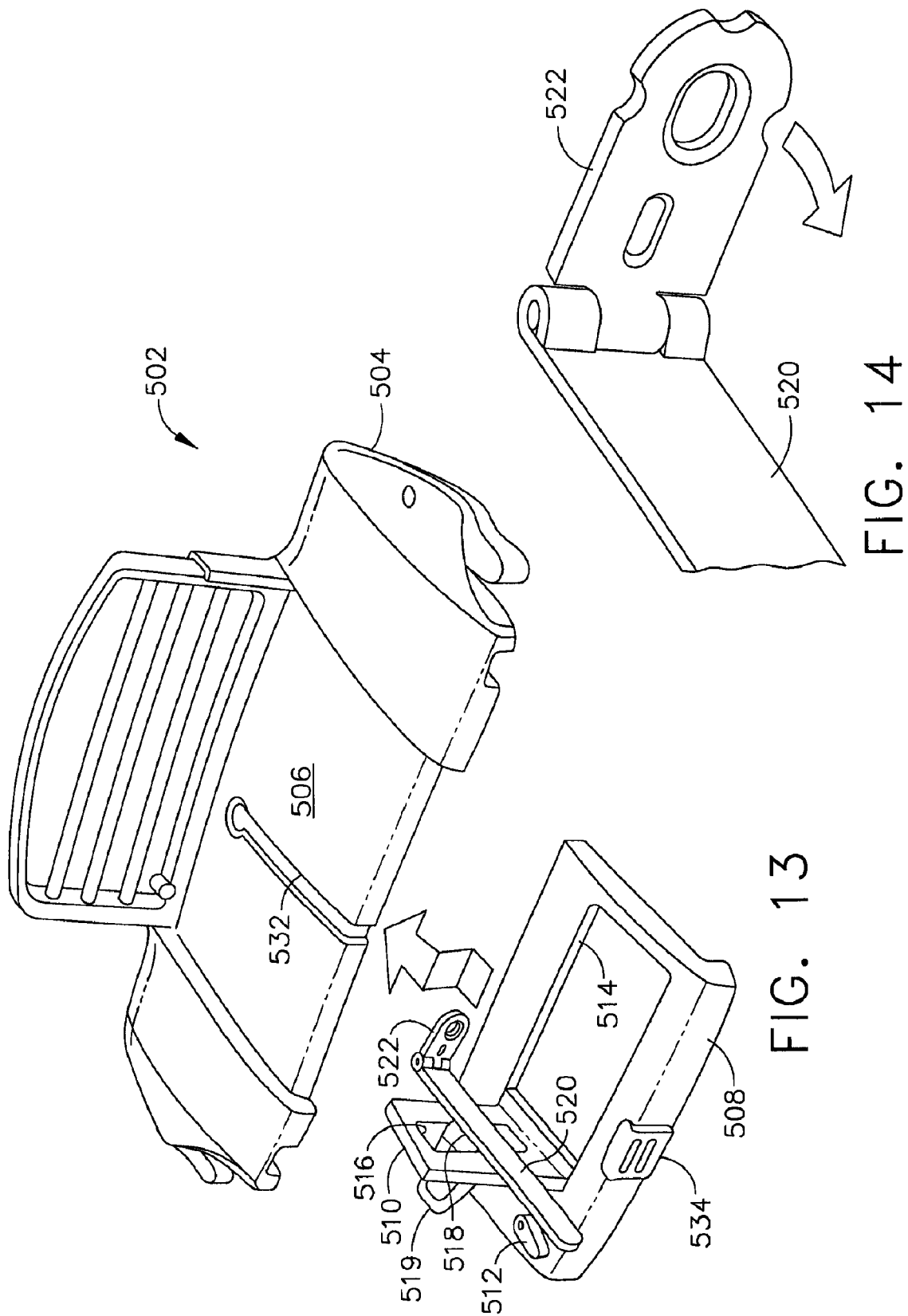

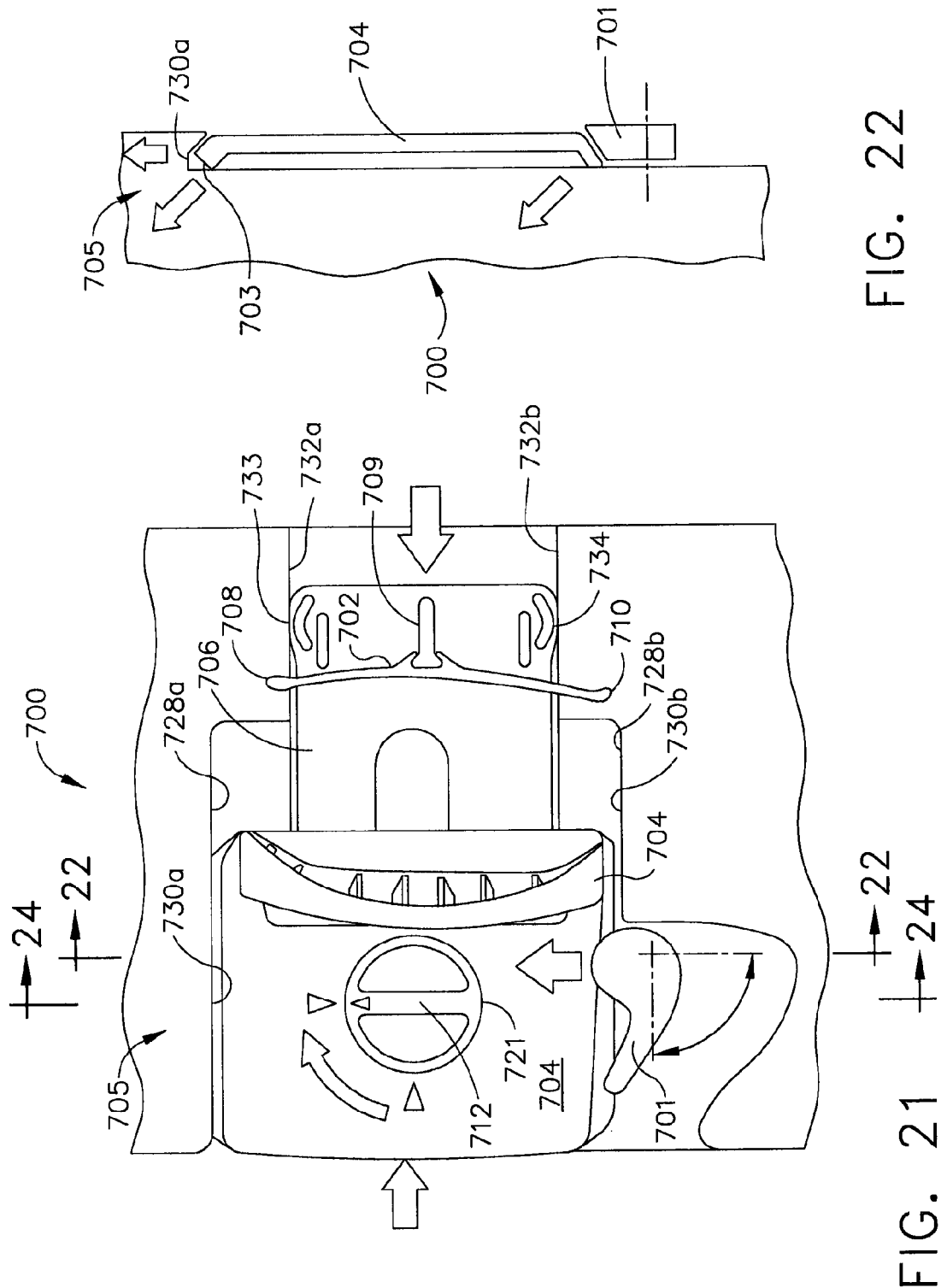

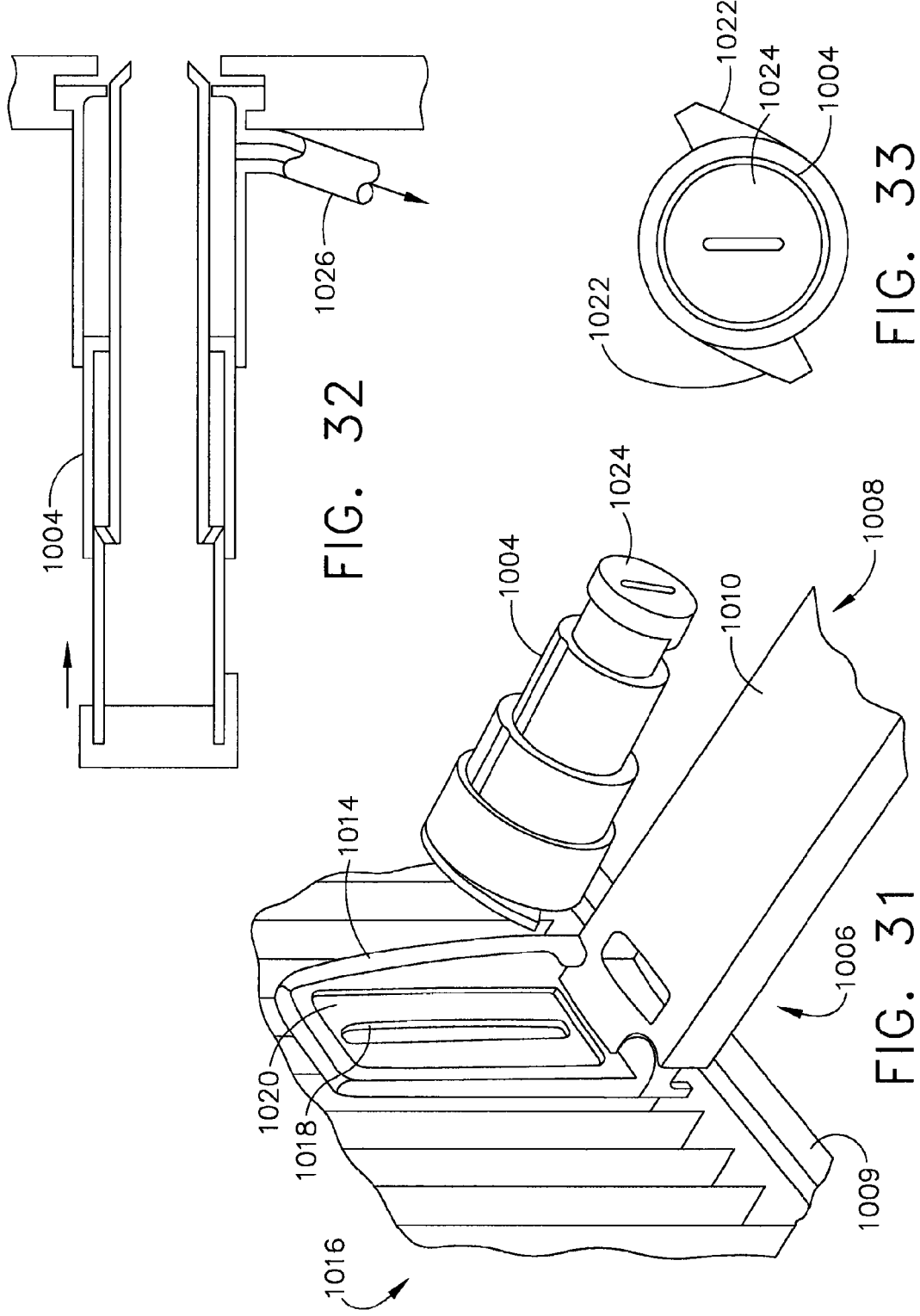

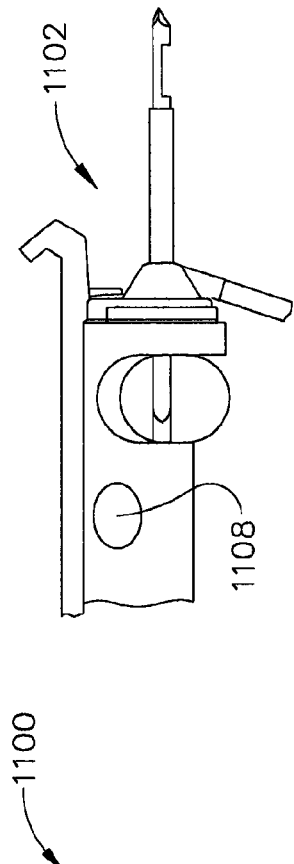
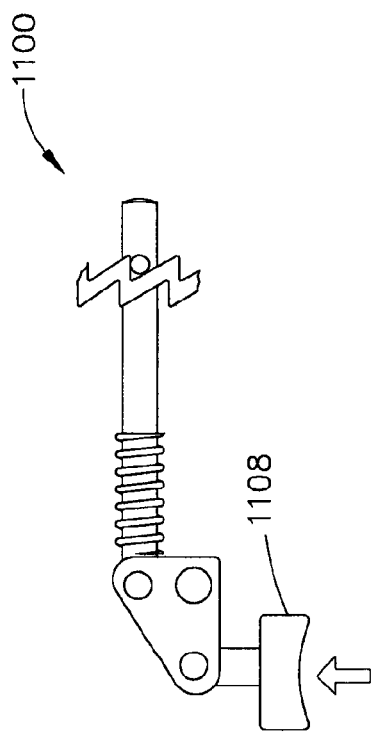
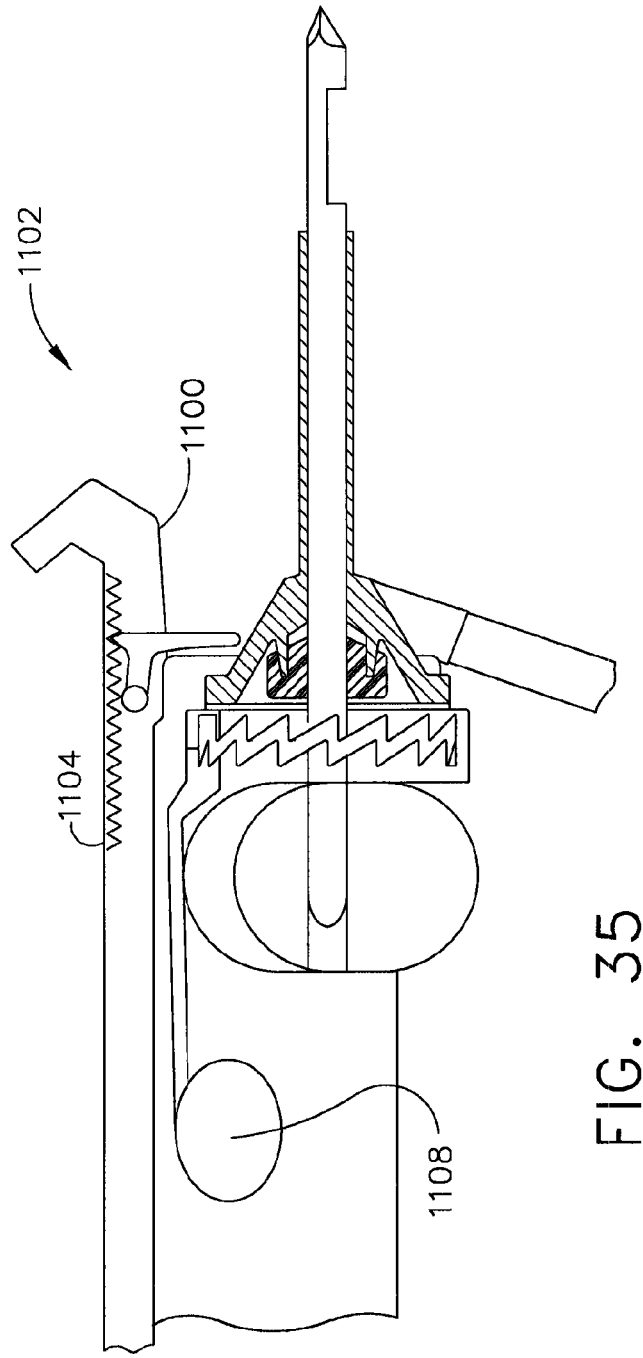
FIG. 34
FIG. 36
FIG. 35

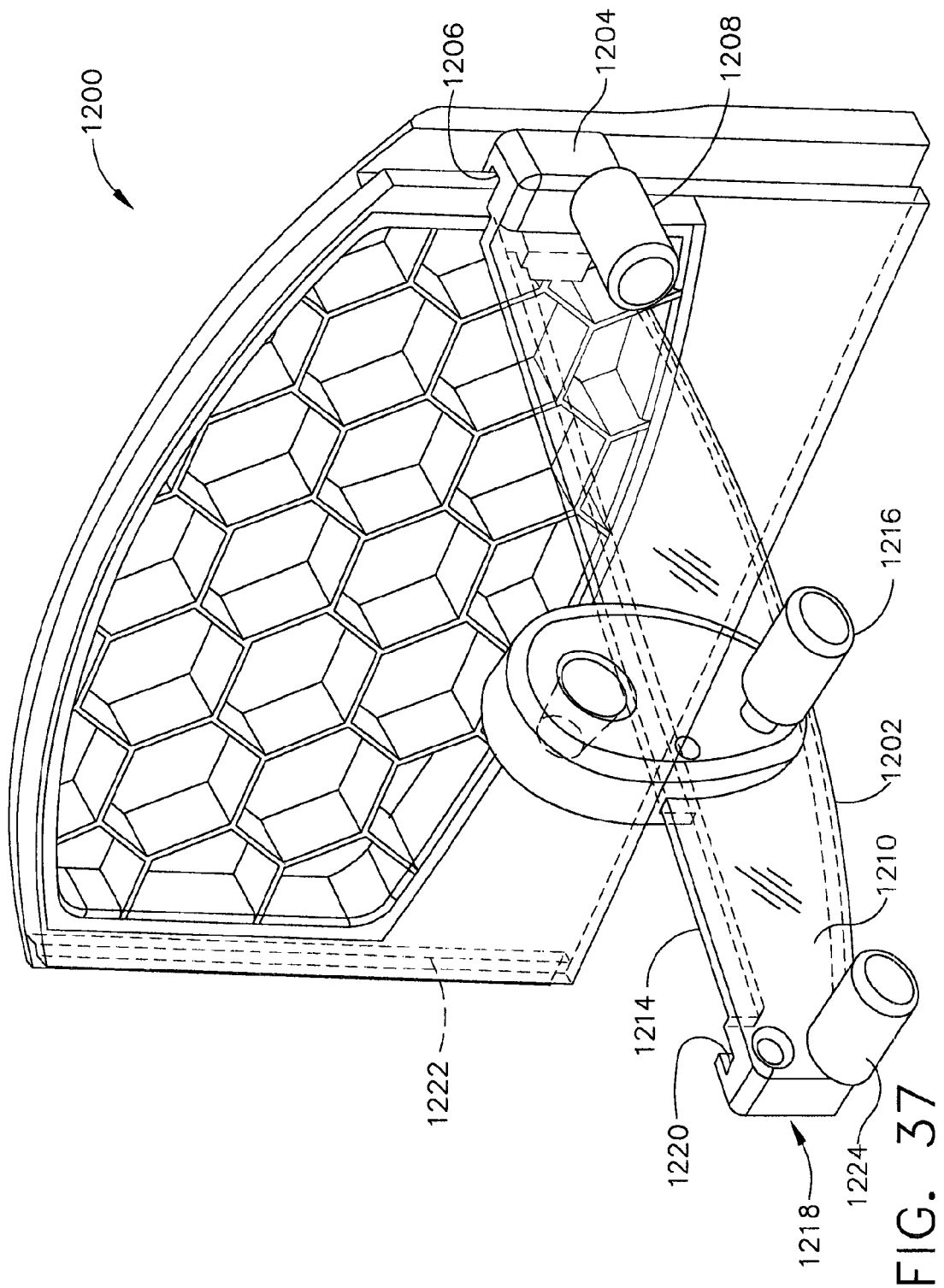

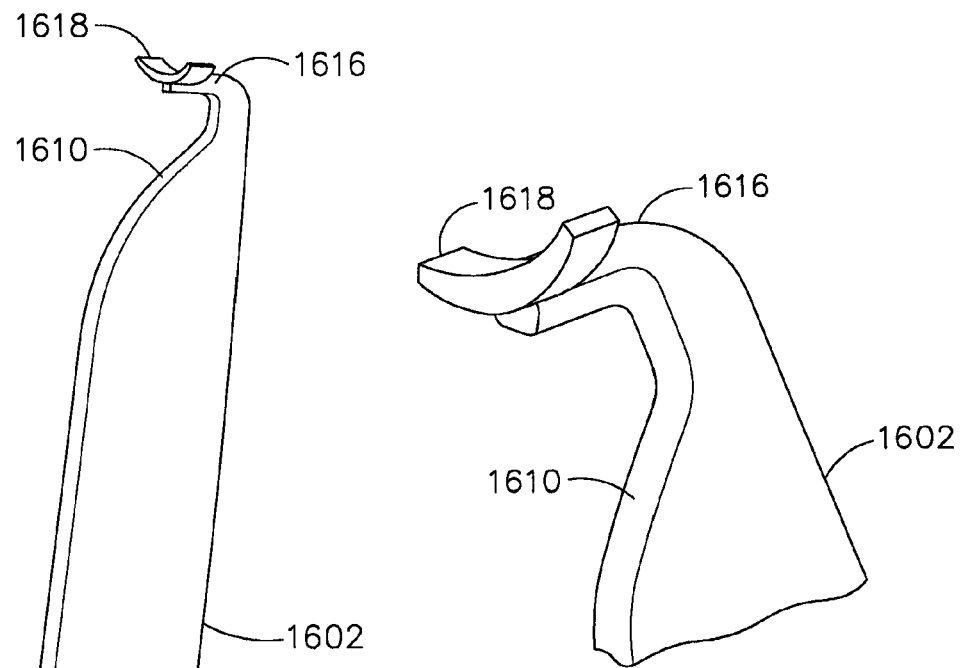
FIG. 45
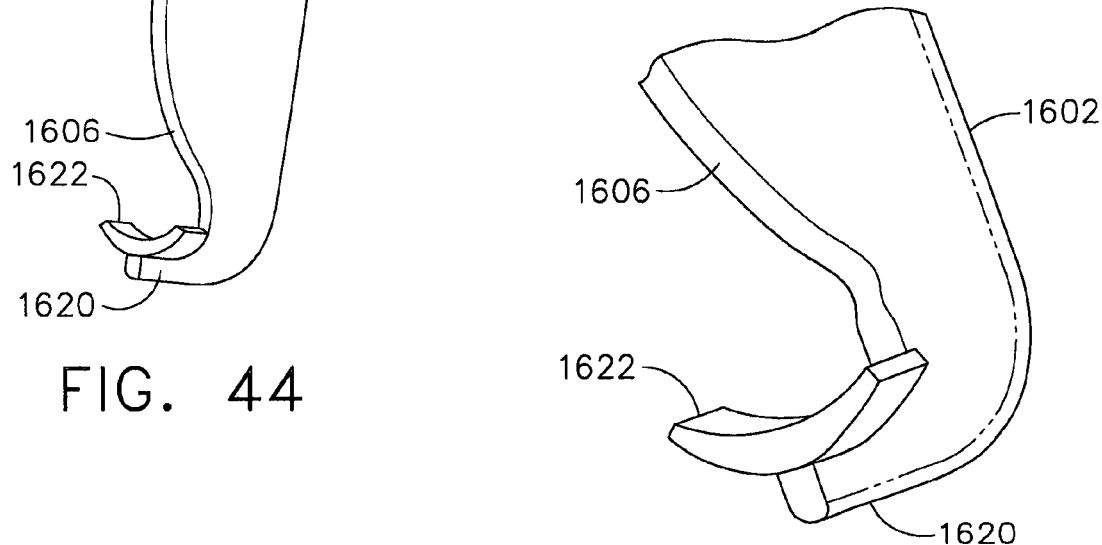
FIG. 44
FIG. 46

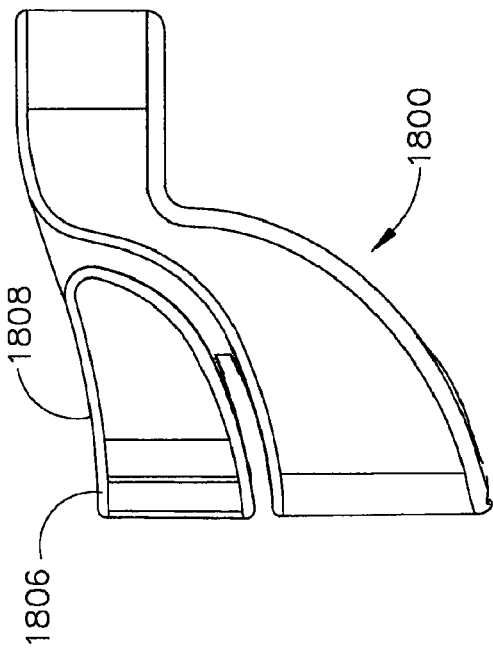
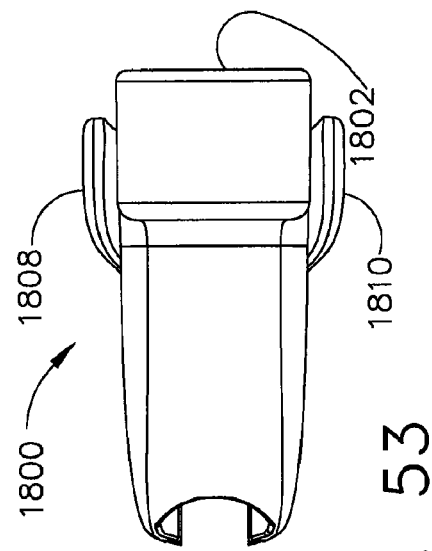
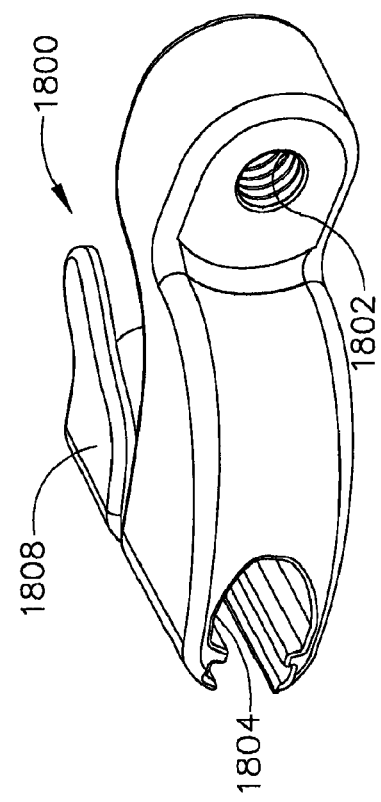
FIG. 50
FIG. 51
FIG. 52
FIG. 53

MRI BIOPSY DEVICE LOCALIZATION FIXTURE

CROSS REFERENCE TO RELATED APPLICATIONS

The present application claims the benefit of U.S. provisional patent application entitled "MRI BIOPSY DEVICE" to Hughes et al., Ser. No. 60/573,510, filed on May 21, 2004, the disclosure of which is hereby incorporated by reference in its entirety.

FIELD OF THE INVENTION

The present invention relates, in general, to a method of imaging assisted tissue sampling and, more particularly, to an improved method for positioning a biopsy probe with respect to a magnetic resonance imaging (MRI) breast coil for acquiring subcutaneous biopsies and for removing lesions.

BACKGROUND OF THE INVENTION

Recently, core biopsy devices have been combined with imaging technology to better target a lesion in breast tissue. One such commercially available product is marketed under the trademark name MAMMOTOME™, by Ethicon Endo-Surgery, Inc. An embodiment of such a device is described in U.S. Pat. No. 5,526,822 issued to Burbank, et al., on Jun. 18, 1996, and is hereby incorporated herein by reference. Its handle receives mechanical and electrical power as well as vacuum assist from a remotely positioned control module that is spaced away from the high magnetic field of a Magnetic Resonance Imaging (MRI) machine.

As seen from that reference, the instrument is a type of image-guided, percutaneous coring, breast biopsy instrument. It is vacuum-assisted, and some of the steps for retrieving the tissue samples have been automated. The physician uses this device to capture "actively" (using the vacuum) the tissue prior to severing it from the body. This allows the sampling of tissues of varying hardness. In addition, a side opening aperture is used, avoiding having to thrust into a lesion, which may tend to push the mass away, cause a track metastasis, or cause a hematoma that, with residual contrast agent circulating therein, may mimic enhancement in a suspicious lesion. The side aperture may be rotated about a longitudinal axis of the probe, thereby allowing multiple tissue samples without having to otherwise reposition the probe. These features allow for substantial sampling of large lesions and complete removal of small ones.

In the aforementioned Pub. No. US 2003/0199785 to Hibner et al., localization fixtures are described that are attachable to a breast coil. These localization fixtures aided in accurately positioning the probe to a location of a suspicious lesion within breast tissue. In particular, the X-Y-Z Cartesian coordinates of a suspicious lesion are referenced to a fiduciary marker in the localization fixture. Humanly visible measurement guides for each axis then allow the probe to be correspondingly positioned after a patient has been withdrawn from a closed bore MRI machine without the need for imaging the probe during insertion. In addition, the localization fixture enabled use of a detachable probe of an MRI biopsy device. Thus, during subsequent reimaging of the probe, a handle of the MRI biopsy device may be deattached, as may be necessary within the close confines of a closed bore MRI machine. When the handle is attached to the probe, various support structures of the localization fixture are described that support the ended length of the handle.

While a localization fixture used with a detachable MRI biopsy probe has a number of advantages, it is desirable to incorporate additional features that further assist in efficiently and comfortably localizing the breast of a patient within a localization fixture by supporting various biopsy devices in a hands-free manner.

BRIEF SUMMARY OF THE INVENTION

The invention overcomes the above-noted and other deficiencies of the prior art by providing a localization and guidance assembly that interfaces an MRI biopsy device to a breast coil to accurately position and maintain a probe at a desired position in a patient's breast for performing biopsy and related diagnostic and therapeutic procedures.

In one aspect of the invention, a localization fixture advantageously provides lateral and medial compression members that may be centered on, brought into opposing compression of a patient's breast, and locked in this position with access to proximal controls that avoid the inconvenience and discomfort of having to reach under the patient. Thereby, a stressful medical procedure is rendered a little easier for the patient and expedited for the care provider.

In another aspect of the invention, a fiducial for locating a suspicious lesion relative to the localization fixture is made more economical by providing a disposable housing that may be shipped without an MRI imagable material. Thereby, shelf-life, packaging, sterility are simplified, as well as allowing the end user to select an appropriate content. The disposable fiducial is engagable to the biopsy probe support.

In yet another aspect of the invention, a localization fixture has a removable tray adjustable that supports a biopsy probe support. Thus, a desired insertion point relative to the lateral compression member may be remotely set on the biopsy probe support prior to locking the removable tray to the base member.

In yet a further aspect of the invention, a localization fixture has a pedestal that is positioned for lateral movement relative to a lateral plate that positions a lateral fence for compressing one side of a patient's breast. A guide rail is positionable upon the pedestal to set a height coordinate. The targeting rail includes a biopsy guide defining an angle of penetration for a biopsy instrument.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 7 is a left side view in elevation of an obturator with a flat bladed piercing tip, lumen communicating between a lateral notch and fluid fitting on a proximal end with external engaging features for an obturator hub;

FIG. 8 is a front view in elevation of the obturator of FIG. 7;

FIG. 9 is a left side view in elevation of a longitudinal cross section of the obturator of FIG. 8 taken along lines 9-9;

FIG. 10 is a front view in elevation of the obturator of FIG. 7 taken in cross section along lines 10-10 distal to a hub engaging portion;

FIG. 11 is a front view in elevation of the obturator of FIG. 7 taken in cross section along lines 11-11 across the hub engaging portion;

FIG. 13 is a perspective view of a localization fixture having a pivoting z-stop integral to a track;

FIG. 14 is a perspective detail view of the z-stop of FIG. 13.

FIG. 21 is a top view of a localization fixture with a proximal medial plate locking control, flexible/curved medial fence and lateral plate, and flexible cam locked lateral assembly;

FIG. 22 is a front cross sectional view in elevation of a lateral plate and top recess of a base plate of the localization fixture of FIG. 21 taken along lines 22-22;

FIG. 31 is a perspective, detailed view of a telescoping targeting ring of FIG. 30 detached from an X-Y alignment fixture;

FIG. 32 is a top cross sectional view of the telescoping targeting ring of FIG. 31 attached to the X-Y alignment fixture and showing a pneumatic outlet and septum;

FIG. 33 is a front view in elevation of the septum of the telescoping targeting ring of FIGS. 31-32;

FIG. 34 is a top view of a remotely rotated localization fixture for the MRI biopsy system of FIG. 1;

FIG. 35 is top view in cross section of the remotely located localization fixture of FIG. 34;

FIG. 36 is a detailed view of a rotation control mechanism of the remotely located localization fixture of FIG. 35;

FIG. 37 is a perspective view of a honeycomb lateral plate with an integral distal targeting fixture shown in its swung open position;

FIG. 44 is a back, left perspective view of a detached bar of the lateral fence of FIG. 43;

FIG. 45 is a detailed perspective view of an upper portion of the detached bar of FIG. 44;

FIG. 46 is a detailed perspective view of a lower portion of the detached bar of FIG. 44;

FIG. 50 is proximal perspective view of an alternative fiducial holder;

FIG. 51 is a top view of the alternative fiducial holder of FIG. 51;

FIG. 52 is a proximal side view in elevation of the fiducial holder of FIG. 51;

FIG. 53 is a right side view in elevation of the fiducial holder of FIG. 51;

DETAILED DESCRIPTION OF THE INVENTION

Figure 1:
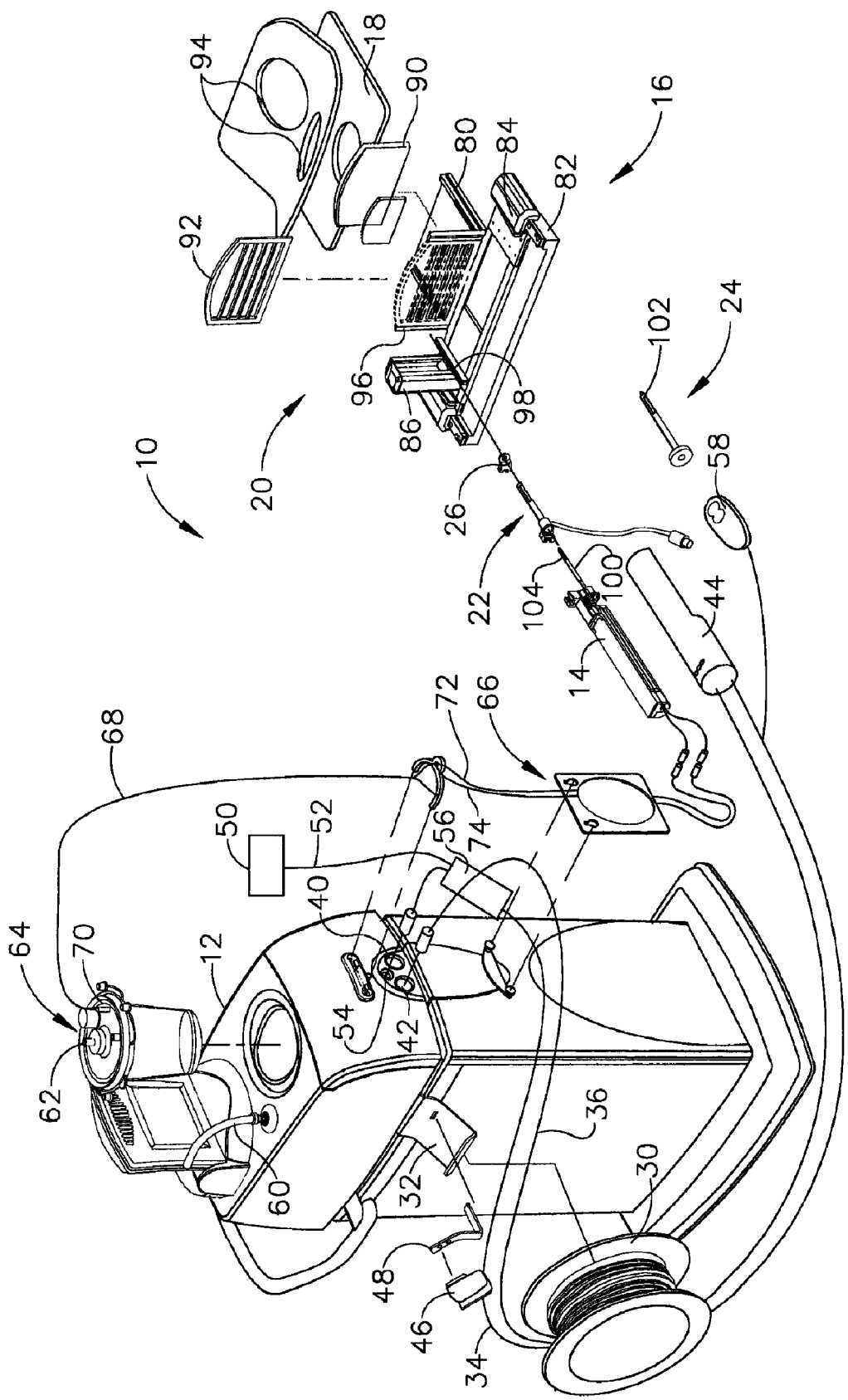
FIG. 1 is a perspective disassembled view of a Magnetic Resonance Imaging (MRI) Biopsy System.

Turning to the Drawings, wherein like numerals denote like components throughout the several views, in FIG. 1, a Magnetic Resonance Imaging (MRI) compatible biopsy system 10 includes a guide that guides a sleeve and introducer obturator that are separate from the biopsy device itself and advantageously incorporate an improved piercing portion, MRI imaging marker, and fluid handling capabilities. Mounting provisions allow for precise penetration along a desired trajectory without overshooting.

The MRI compatible biopsy system 10 includes a control module 12 that typically is placed outside of a shielded room containing an MRI machine (not shown) or at least spaced away to mitigate detrimental interaction with its strong magnetic field and/or sensitive radio frequency (RF) signal detection antennas. The control module 12 controls and powers an MRI biopsy device 14 that is compatible for use in close proximity to the MRI machine. An example of an MRI biopsy device 14 is the afore-mentioned MAMMOTOME™ instrument. The MRI biopsy device 14 is accurately positioned by a localization fixture 16 that is attached to a breast coil 18, which in turn supports a patient (not shown). Examples of commercially available breast coils 18 include the BIOPSY BREAST COIL MODEL BBC by MRI DEVICES CORPORATION of Waukesha Wis. A guidance assembly 20, and in particular a sleeve 22, advantageously attaches to the localization fixture 16 to increase imaging and therapeutic flexibility and accuracy in conjunction with selective use of the MRI biopsy device 14 at particular parts of the procedure. The guidance assembly 20 may include one or more obturators 24 with one depicted that seals the sleeve 22 during insertion and during subsequent portions of the procedure in which the MRI biopsy device 14 is not inserted therein. A depth stop 26 is provided for use with the localization fixture 16 to advantageously prevent over-insertion of the sleeve 22, inadvertent retraction of the sleeve 22 and/or to enhance accurate placement of the sleeve 22 to a desired location along the Z-Axis.

For convenience, herein a convention is used for locating a suspicious lesion by Cartesian coordinates within breast tissue referenced to the localization fixture 16 and to thereafter position an instrument (e.g., sleeve 22) to this location without necessarily continuously imaging the region. As will be described in greater detail below, a perforated barrier that is compressed along an outside side of the breast, with respect to a medial plane of the chest of the patient, defines an X-Y plane, with the X-axis being vertical (sagittal) with respect to a standing patient and which corresponds to a left to right axis as viewed by a clinician facing the externally exposed portion of the localization fixture 16. A fiduciary marker (not shown), attached to or positioned relative to the localization fixture 16 proximate to the patient's skin, defines the origin of this plane. Perpendicular to this X-Y plane extending toward the medial side of the breast is the Z-axis, which typically corresponds to the orientation and depth of insertion of the MRI biopsy device 14, although it should be appreciated that variations may allow insertion at an angle to this Z-axis. Thus, for clarity, the term Z-axis may be used interchangeably with "axis of penetration", although the latter may or may not be orthogonal to the spatial coordinates used to locate an insertion point on the patient.

Separating the tracking rail that supports a mount/depth stop from a biopsy rail that supports the weight of the biopsy device advantageously reduces interference between the various components, allowing a sequence of operation wherein certain components may be selectively installed and removed without interfering with other components.

In use, the MRI compatible biopsy system 10 is prepared for use by placing a cable management spool 30 upon a cable management attachment saddle 32 that projects from a side of the control module 12. Wound upon the cable management spool 30 is a paired electrical cable 34 and mechanical cable 36 for communicating control signals and cutter rotation/advancement motions respectively. In particular, electrical and mechanical cables 34, 36 each have one end connected to respective electrical and mechanical ports 40, 42 in the control module 12 and another end connected to a holster 44 that receives the MRI biopsy device 14. An MRI docking cup 46, which may hold the holster 44 when not in use, is hooked to the control module 12 by a docking station mounting bracket 48.

An interface lock box 50 mounted to a wall provides a tether 52 to a lockout port 54 on the control module 12. The tether 52 is advantageously uniquely terminated and of short length to preclude inadvertent positioning of the control module 12 too close to the MRI machine. An in-line enclosure 56 may advantageously register the tether 52, electrical cable 34 and mechanical cable 36 to their respective ports 54, 42, 44 on the control module 12. A remote keypad 58 may be distally connected to the electrical cable 34 to enhance clinician control of the MRI biopsy device 14, especially when controls on the MRI biopsy device 14 itself are not readily accessible after insertion into the localization fixture 16.

Vacuum assist is provided by a first vacuum line 60 that connects between the control module 12 and an outlet port 62 of a vacuum canister 64 that catches liquid and solid debris. A tubing kit 66 completes the pneumatic communication between the control module 12 and the MRI biopsy device 14. In particular, a second vacuum line 68 is connected to an inlet port 70 of the vacuum canister 64. The second vacuum line 68 divides into two vacuum lines 72, 74 that are attached to the MRI biopsy device 14. With the MRI biopsy device 14 installed in the holster 44, the control module 12 performs a functional check. Saline is manually injected into biopsy device 14 to serve as a lubricant and to assist in achieving a vacuum seal. The control module 12 actuates a cutter mechanism (not shown) in the MRI biopsy device 14, monitoring full travel.

The portion of the MRI compatible biopsy system 10 used near the MRI machine is also assembled. The generally known breast coil 18 is placed upon a gantry of the MRI machine, along with other body support pads (not shown). The localization fixture 16 is attached within a recess on either lateral side of the breast coil 18 to access a patient's breast that is pendulously exposed therein and includes a horizontal medial plate 80, a reusable base assembly 82, a lateral assembly 84, and a positioning pedestal 86. The localization fixture 16 is also assembled with a disposable medial fence 90 and a lateral window (or perforated plate) 92.

The base assembly 82 is placed within a selected lateral recess of the breast coil 18. The medial fence 90 attaches to a medial edge of the medial plate 80, aligned vertically approximately along a longitudinal axis of the breast coil 18 under an inner edge of a selected breast aperture 94 that receives a patient's breast. With the patient thus positioned and the outer area of the breast sterilized, the lateral window 92 is downwardly slid into a three-sided frame guide 96 of the lateral assembly 84, which in turn is placed upon the medical plate 80. The base assembly 82 and lateral assembly 84 are moved with respect to one another along the Z-axis to compress the patient's breast between the medial fence 90 and the lateral window 92. A mechanism formed between the lateral assembly 84, base assembly 82, and medial plate 80 maintains this compression.

Contrast agent may be injected into the patient to enhance the imaging. The gantry is advanced into the MRI machine bore to image the localization fixture 16 and breast tissue. The fiduciary marker on the lateral window 92 is located and designated as the origin of the X-Y-Z coordinates. Then a suspicious lesion is located within the image and a point thereon is selected to determine its location relative to the origin. It should be appreciated that orienting the X-Y-Z axis of an initial scan may be facilitated by having the lateral window 92 formed of an imagable material, thus presenting an X-Y plane in addition to the origin point of the fiduciary marker. With the target location determined, the gantry is withdrawn from the MRI machine bore.

The positioning pedestal 86 is slidably engaged along the X-axis of the lateral assembly 84 and defines a vertical guide for positioning a single targeting rail ("track") 98 at a selected Y-axis coordinate. The track 98 in turn provides a depth guide along the Z-axis for positioning the depth stop 26 and the holster 44 at a desired Z-axis coordinate. The depth stop 26 is latched onto the track 98. Thereafter, a marking instrument (not shown) may be inserted through the depth stop 26 to mark the insertion point on the breast. Thereafter, the depth stop 26 is moved out of the way. Anesthesia is injected superficially, followed by a scoring cut at the marked location and a subsequent injection of anesthesia more deeply into the scored cut. The depth stop 26 is then repositioned on the track 98 to the desired Z-axis coordinate reference.

The obturator 24 is inserted into the sleeve 22 and may be positioned to close any apertures of the sleeve 22 (side and/or distal end) to present a closed surface to the breast tissue. The obturator may also be shaped or formed to enhance the visibility of the aperture location. One or the other of the obturator 24 and sleeve 22 presents a sharp tip (not shown) to penetrate breast tissue. For instance, if using a sleeve 22 having an open end, an obturator may provide a sharp tip.

The obturator 24 is inserted into the sleeve 22 and the combination is guided by the track 98 to a proper orientation until an accurate depth is reached as set by the depth stop 26. Once fully inserted, the depth stop 26 prevents over-insertion. The sleeve 22 advantageously latches to the track 98 and/or the depth stop 26 to prevent inadvertent retraction, such as when the obturator 24 is withdrawn, and pressure is received from the breast tissue or later when a probe 100 of the MRI biopsy device 14 is withdrawn from the sleeve 22.

The gantry is moved into the MRI machine bore and the patient is imaged again to confirm placement of the sleeve 22 with respect to the suspicious lesion. Advantageously, imagable materials of the sleeve 22 and/or obturator 24, perhaps comprising or including marker material, enhance the ability to confirm the location of the sleeve 22 and its sleeve side aperture 102 as positioned for subsequent biopsy samples.

Figure 2:
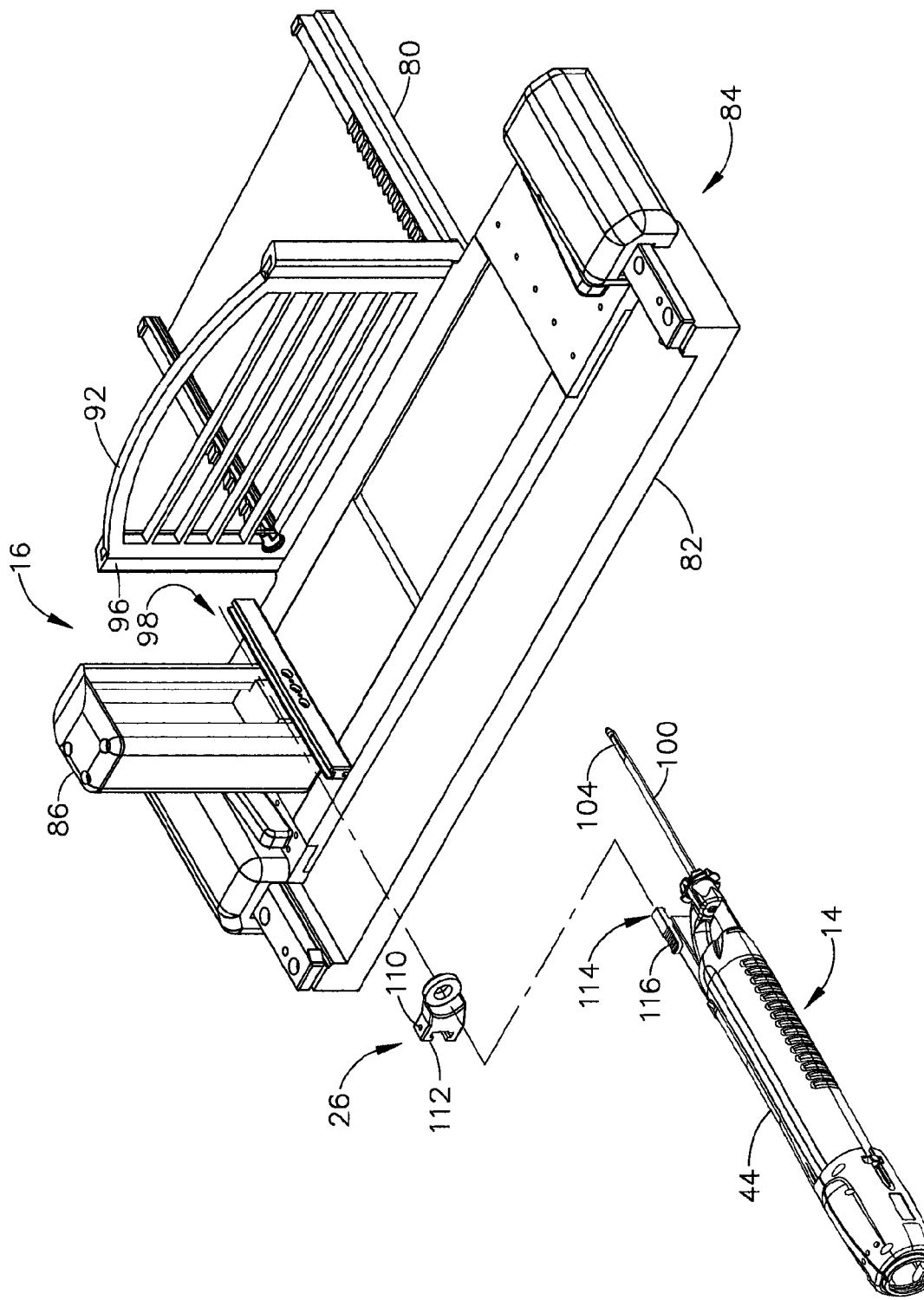
FIG. 2 is a perspective view of a holstered MRI biopsy device being aligned with a track of a pedestal of a localization fixture of the MRI biopsy system of FIG. 1.
Figure 3:
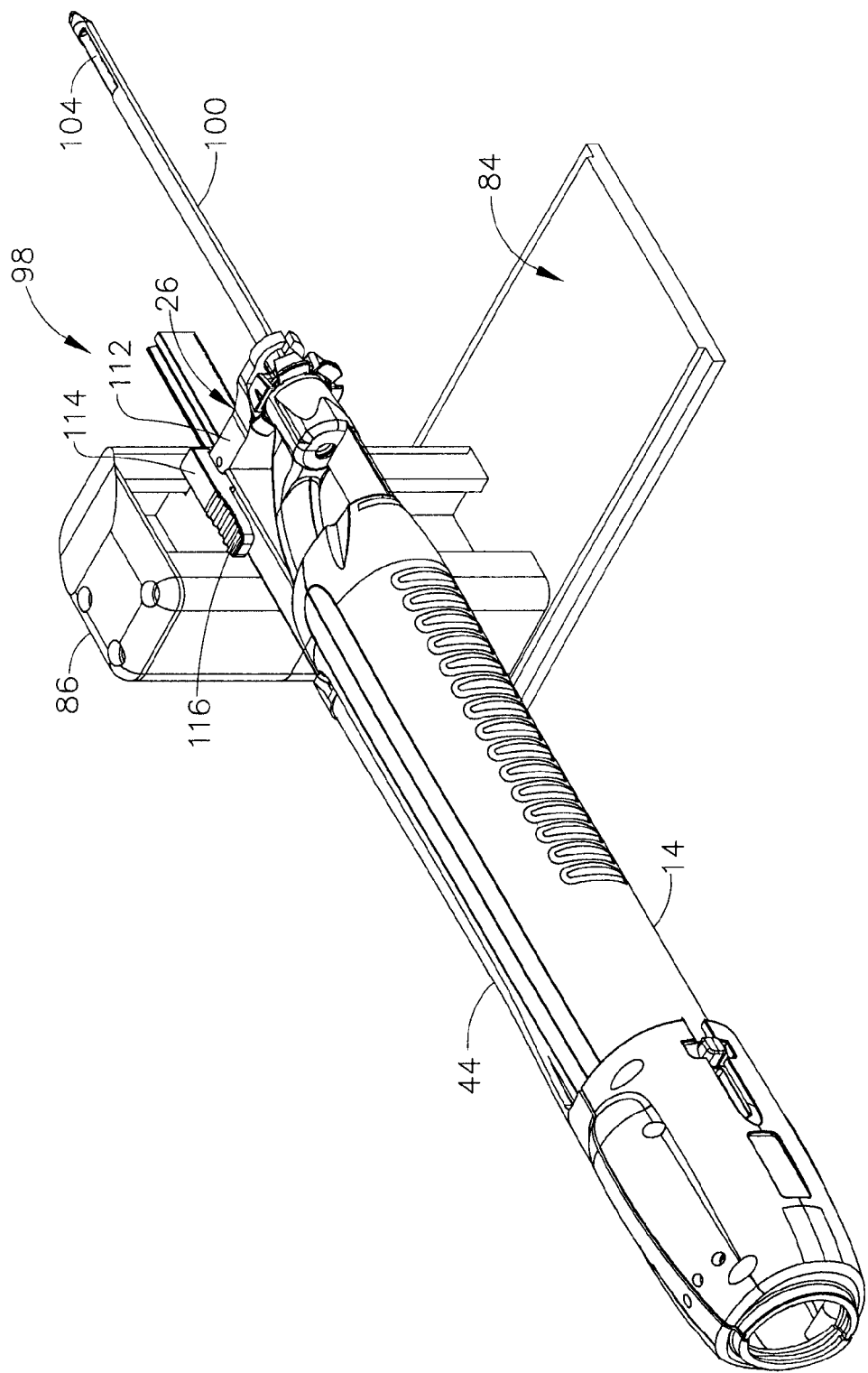
FIG. 3 is a perspective view of the holstered MRI biopsy device after engagement to the track of the pedestal of the localization fixture of the MRI biopsy system of FIG. 1.

The patient is removed from the MRI machine by retracting the gantry and the holstered MRI biopsy device 14 is brought to the localization fixture 16. A protective cap (not shown) is removed from the probe 100 of the MRI biopsy device 14 and the obturator 24 is removed from the sleeve 22. Mounting of the holster 44 to the track 98 is shown in FIGS. 2 and 3, wherein the holster 44 and MRI biopsy device 14 combination slide onto the track 98 that has been positioned at a certain location with respect to the pedestal 86 and lateral assembly 84. Features of the sleeve 22 and probe 100 may advantageously visually and mechanically orient a probe side aperture 104 of the probe 100 with the sleeve side aperture 102, as well as forming a gas seal. Advantageously, the holster 44 and/or the probe 100 may latch onto the track 98 or sleeve 22 to confirm full insertion and prevent over-insertion and inadvertent retraction. The holster 44 allows an MRI biopsy device 14 intended for handheld use to have sufficient support in its attachment to the localization fixture 16 to accurately maintain its position and to avoid or minimize loads carried by the probe 100.

Thereafter, the MRI compatible biopsy system 10 may take tissue samples by activating a cutter mechanism in conjunction with vacuum assist, withdrawing the cutter and withdrawing a tissue sample, the latter perhaps also with vacuum assist. The probe 100/sleeve 22 combination are capable of manual, or perhaps automatic, rotation to a desired angle with respect to their longitudinal axis for additional samples or additional samples may be taken at the current orientation by further resorting to vacuum assist. The cutter is then advanced to close the probe side aperture 104 and the holster 44 is withdrawn from the localization fixture 16, thereby removing the probe 100 from the sleeve 22.

Additional steps or combinations of steps may be performed at this point such as using the probe 100, a specialized obturator 24 (e.g., stylet), or merely the sleeve 22 to guide various agents to the surgical site of the biopsy. Examples include draining fluids, inserting anesthetic agents, inserting hemostatic agents, insufflating with pneumatic pressure and inserting a marker for subsequently locating the site of the biopsy, or other diagnostic or therapeutic procedures.

The patient is then typically drawn back into the MRI machine bore for reimaging to confirm removal of at least a portion of the suspicious lesion and possibly placement of a marker. During this reimaging, the sleeve 22 is sealed with the obturator or stylet 24. Thereafter, the localization fixture 16 is removed, the patient bandaged and removed from the gantry, and the disposable portions of the MRI compatible biopsy system 10 disposed of as medical waste.

With particular reference to FIGS. 2-3, the single targeting rail 98 facilitates sequential mounting of separate components. First the depth stop 26, then the sleeve 22 (as in FIG. 1), and then the biopsy tool 14 is slid onto the single targeting rail 98. Alternatively as depicted in FIGS. 2-3, the single targeting rail 98 may receive the depth stop 26 and then an MRI biopsy device 14 is used without a separate sleeve 22. The maximum depth of penetration into the patient's breast is preset by the location of the depth stop 26 on the single targeting rail 98. An engagement mechanism between the holster 44 and the single targeting rail 98 (not shown) and/or an engagement mechanism formed by a catch, is depicted as an upwardly projecting pin 110, on an upper rail-gripping arm 112 of the depth stop 26 and a downwardly spring-biased rocker latch 114 that snaps onto the upwardly projecting pin 110, preventing inadvertent retraction of the MRI biopsy device 14. The holster 44 may be disengaged by downward pressure on a proximal actuating arm 116 of the rocker latch 114.

The single targeting rail 98 may be longitudinally sized to be proximally extending sufficient that the MRI biopsy device 14 engages the single targeting rail 98 prior to the probe 100 contacting the patient's skin. The single targeting rail 98 is also sized to not extend proximally so far as to preclude use in a closed bore MRI machine (not shown). Such an MRI compatible biopsy system 10 is believed to minimize the procedure turn-around time to less than 45 minutes as described above. Despite this expeditious turn-around, a radiologist may position the probe 100 accurately to within 2 mm (5 mm maximum) of the lesion center. Further, the radiologist may maximize access to both breasts (left or right) during a procedure (both sides of the table) with minimal repositioning of the patient. Further, a minimal amount of force is required to penetrate tissue, such as less than 4 lbs. Although the depth stop 26 serves to prevent overshooting, features for repositioning the depth stop 26 prior to further insertion of the probe 100 allow clinical flexibility in targeting another location.

Figure 4:
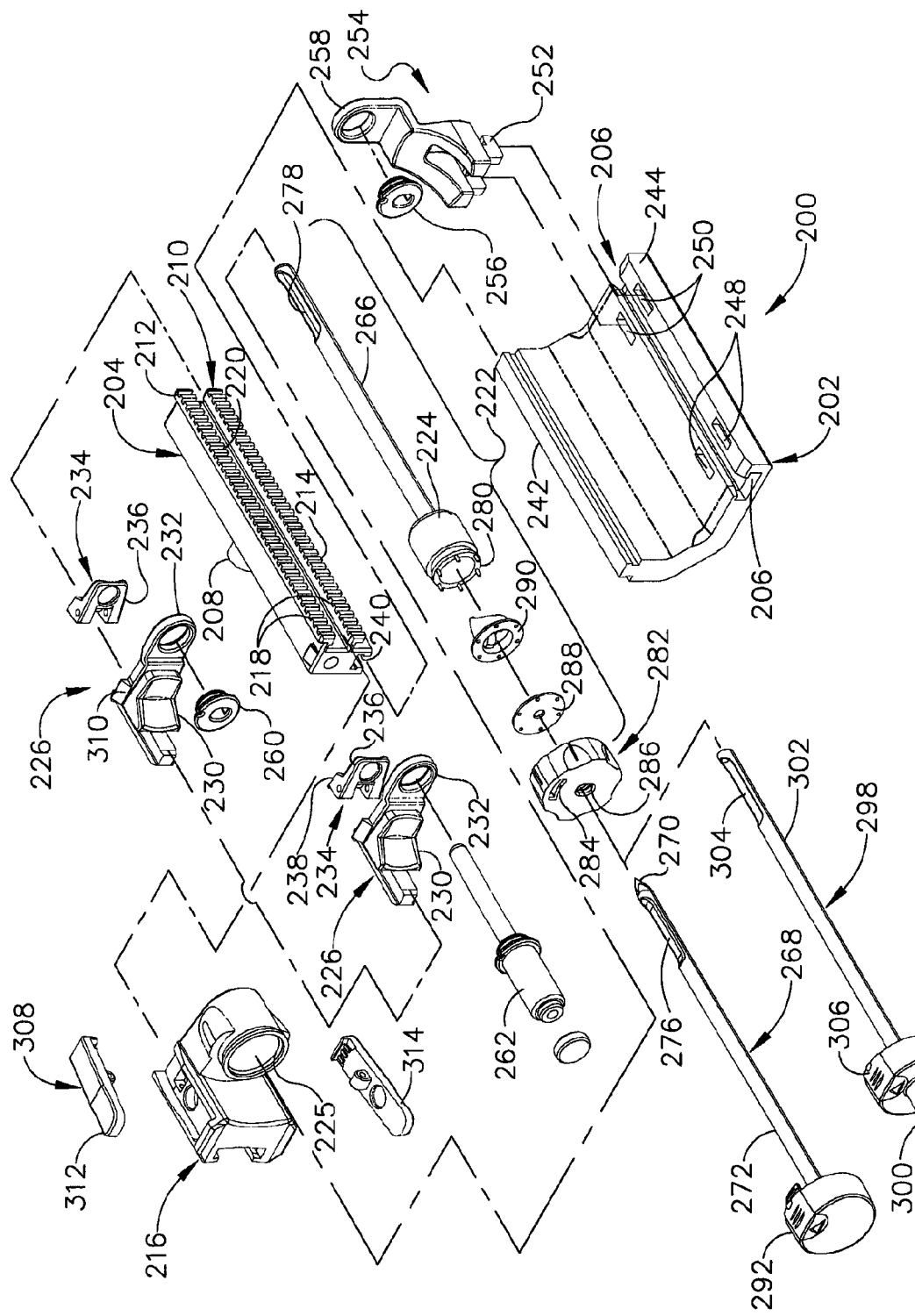
FIG. 4 is a perspective view of a disassembled view of a guidance system of the localization fixture of FIG. 1.

In FIG. 4, an alternative guidance assembly 200 for the MRI compatible biopsy system 10 incorporates a cradle 202 that attaches to a targeting rail 204 and provides a biopsy rail 206 for supporting the MRI biopsy device, both rails 204, 206 aligned to the Z axis. The targeting rail 204 is attached to the positioning pillar 86 (not shown in FIG. 4) and vertically adjusted to a desired Y-position. A circular attachment point 208 may form a rotational engagement to the positional pedestal 86 to allow an angled targeting guide.

A lateral face 210 of the targeting rail 204 includes an upper flange 212 and a lower flange 214, each having an L-shaped cross section for slidingly receiving a sleeve mount 216. Vertical rows of laterally projecting ridges 218 in each flange 212, 214 serve as a locking surface for the sleeve mount 216. Between the flanges 212, 214, a side channel 220 is recessed therein. The sleeve mount 216 guides a sleeve 222 by having its sleeve hub 224 proximally received in a hub receptacle 225 of the sleeve mount 216 and distally positioned and constrained by a depth stop 226.

The depth stop 226 includes a slide member 228 that engages the side channel 220. A depth stop housing 230 attaches thereto, terminating in a reticule 232. A locking lever 234 is vertically pinned within a distally open recess (not shown) defined in the depth stop 226 with a lateral portion 236 spring biased away therefrom such that distally projecting feet 238 pivot against and engage the ridges 218, especially against a proximal movement. Depressing the lateral portion 236 proximally against the distally open recess of the depth stop housing 230 releases the distally projecting feet 238 to allow repositioning the depth stop 226 distally.

An axis of penetration of the biopsy device 10 is aligned with the axes defined by the targeting rail 204 and the biopsy rail 206, which are laterally and vertically orthogonally offset therefrom, respectively. Extending a horizontal plane from the targeting rail 204 and extending a vertical plane from the biopsy rail 206 intersect at a common centerline that is the axis of penetration. Having the biopsy rail 206 vertically aligned and parallel to the axis of penetration advantageously provides support for the weight of the biopsy device 14 with a minimum of torsion loads that may otherwise create deflections of an inserted distal end. Thereby, even for a relatively heavy and elongated device, positioning and maintaining its distal end is achievable within 5 mm, and even 2 mm, of a desired insertion point. Thereby, a "hands free" procedure may be performed, and the inconvenience or the impracticability of penetration in the illustrative version may be replaced by one vertically displaced above the axis of penetration. In particular, having a cradle that may be engaged to either side of the targeting rail 204 would provide further vertical symmetry to take full advantage of the space afforded by the breast coil 18.

While a "hands free" capability is advantageous for a single insertion/multiple sample biopsy device, it should be appreciated that such penetration guidance with a preset depth stop as described herein has application to even lightweight biopsy devices that employ a core needle biopsy with a single insertion per single sample. In particular, correct placement need not be conditional on continuous imaging. Over penetration during insertion and inadvertent displacement is avoided when hands are free.

A bottom dovetail channel 240 in the targeting rail 204 receives a top dovetail extension 242 on the cradle 202, which is slid therein. It should be appreciated that mounting is shown herein on the right side of the positioning pedestal 86 when viewed proximally, but that the guidance assembly 200 advantageously comprises symmetric parts that allow mounting and use on either side of the positioning pedestal 86 to increase flexibility in positioning the probe 100. Thus, a horizontal base 244 of the cradle 202 forms the biopsy rail 206 as a biopsy guide channel 246 flanked by a first and second pair of monocle receptacles 248, 250 so that a pair of locking hooks 252 on a monocle 254 may be inserted in either pair of monocle receptacles 248, 250, depending on which is closer to the patient. Rather than mounting the cradle 202 to the targeting rail 204 as depicted, the cradle may be directly attached to the positioning pedestal 86 (not shown). The cradle 202 is mechanically robust and can support the gross weight of the MRI biopsy device 14. Since the MRI biopsy device 14 does not share the cradle 202, the cradle 202 may be optimized to support the MRI biopsy device 14 when either shallow or deep lesions need to be accessed.

A guide bushing 256 inserted in a monocle reticule 258 guides a marking instrument and/or a scoring scalpel (not shown) as an initial step in locating and preparing an insertion point. The monocle 254 may be removed thereafter or left in place to guide the sleeve 222 in addition to the reticule 232 of the depth stop 226, the latter which may also hold a guide bushing 260 for guiding the sleeve 222. Removing the guide bushings 256, 260 allows for the reticules 258, 232 of the monocle 254 and depth stop 226 to guide a larger component, such as a fiducial 262 used for locating a suspicious lesion relative to the guidance assembly 200.

The alignment of the sleeve 222 is maintained by first passing through the hub receptacle 225 of the sleeve mount 216, which receives the sleeve hub 224. In the illustrative version, the sleeve 222 has an open ended shaft 266 for receiving an introducer obturator 268 that includes a piercing tip (e.g., flat blade) 270 at a distal end of solid obturator shaft 272. A beveled recess 276 into the solid obturator shaft 272 is aligned with a sleeve side aperture 278 of the sleeve 222, and thus ultimately of the probe 100 (FIGS. 1-3). The materials of the obturator 268 may be selected to aid in locating the sleeve side aperture 276 of the sleeve 222, which otherwise may be more difficult to visualize and locate in an MRI scan slice.

The sleeve hub 224 has its proximal cylindrical edge 280 attached to a guidance thumbwheel 282 that proximally extends from the hub receptacle 225 of the sleeve mount 216 for rotating the sleeve 222 to position its sleeve side aperture 278 with reference to a visual mark, depicted as a locking slot 284, on the thumbwheel 282 corresponding thereto. The thumbwheel 282 includes a central through hole 286 sealed by a wiper seal 288 and a duckbill seal 290 trapped between the thumbwheel 282 and the proximal cylindrical edge 280 of the sleeve hub 224. Thus insertion of the obturator 268, which includes a locking tab 292 that enters the locking slot 284, closes the central through hole 286 and forms a dynamic seal against the wiper seal 288.

After removing the obturator 268, a stylet 298 may be inserted into the sleeve 222 so that a proximally presented hose nib 300 of the stylet 298 may be used to insufflate the surgical site or used for other purposes such as draining bodily fluids or inserting therapeutic or diagnostic agents through a stylet shaft 302 of the stylet 298 to a stylet side aperture 304 that is aligned with the side aperture 278 of the sleeve 222. The stylet 298 also includes a locking tab 306.

The sleeve mount 216 includes a downwardly spring-biased rocker latch 308 that snaps onto a ramped catch 310 on the depth stop 226, preventing inadvertent retraction of the sleeve 222. The sleeve mount 216 may be disengaged by downward pressure on a proximal actuating arm 312 of the rocker latch 308. An upwardly spring-based rocker latch 314 attached to the bottom of the sleeve mount 216 similarly engages the depth stop 226. Thus, after the depth stop 226 is set on the targeting rail 204 to a desired depth of insertion, the sleeve mount 216 may be distally advanced without overshooting and subsequently be held in place when removing implements therefrom such as the obturator 268, stylet 298, and MRI biopsy device 14.

Figure 5:
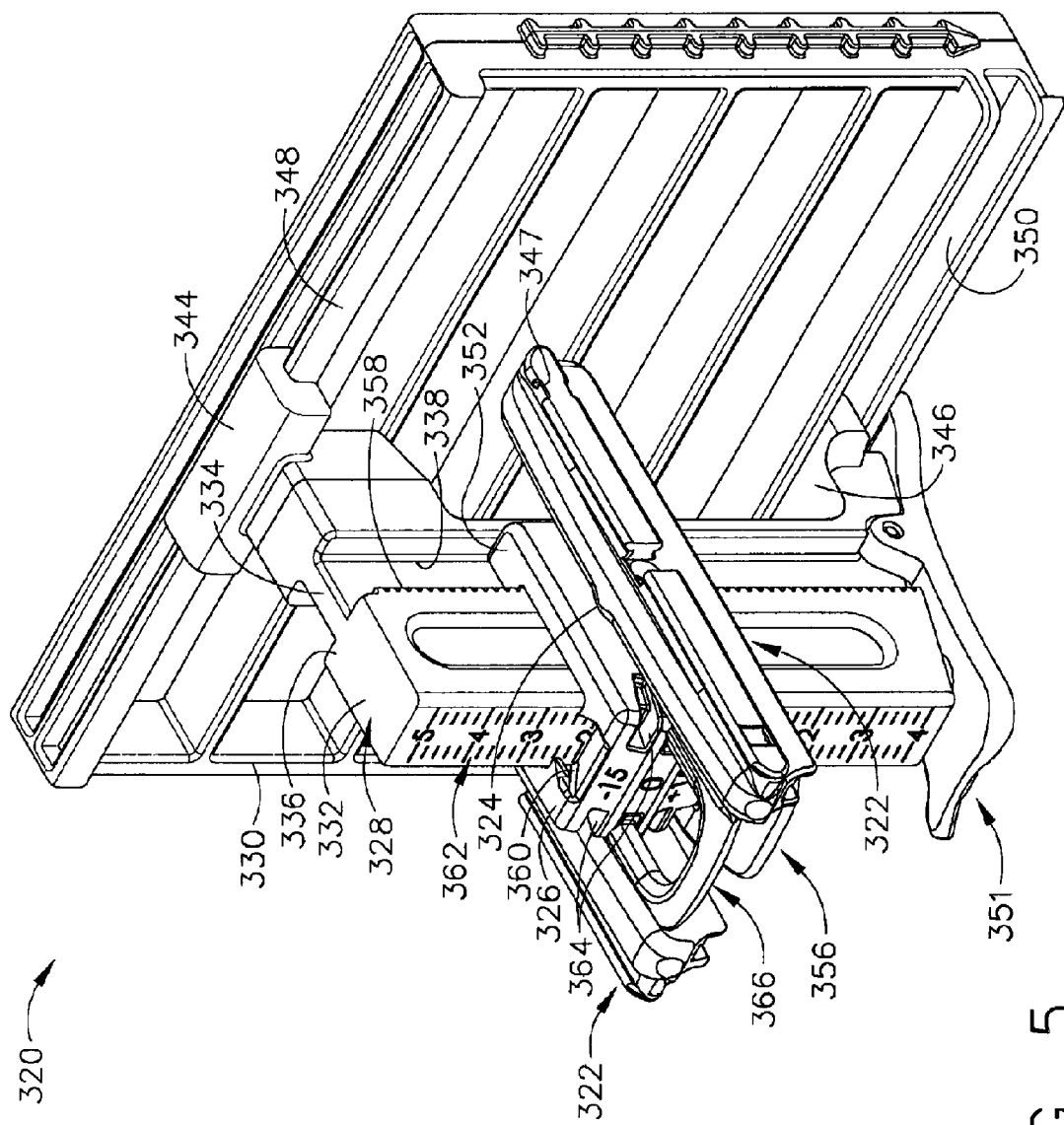
FIG. 5 is a perspective view of an alternative pedestal and targeting rail supported by a lateral fence of a localization fixture for the MRI biopsy system of FIG. 1.

In FIG. 5, a lateral fence supported pedestal 320 provides an alternative support for spatially positioning a primary targeting rail 322 that in turn guides insertion of the sleeve 22 or other piercing biopsy devices (not shown in FIG. 5). The primary targeting rail 322 includes an attachment axle 324 that received in either a left or right side axle hub (not shown) of a (Y-axis) height yoke 326 that is vertically adjustable upon a pedestal 328 that in turn is laterally adjustable upon a lateral fence 330. The pedestal 328 includes a proximal upright rectangular column 332 with a thinner wall 334 projecting from its distal side that flares laterally outward (defining left and right vertical rectangular slots 336, 338) as part of a bracket 340 with top and bottom hanger arms 344, 346 that slide laterally respectively on a top track 348 and a bottom track 350 formed in the lateral fence 330. A lateral (X-axis) adjustment lever 351 may be raised to lift the pedestal 328 and thus the hanger arms 344, 346 out of engagement to the tracks 348, 350 as the lateral adjustment lever 351 is repositioned to the left or right to a desired location with reference to a lateral measurement guide (not shown).

The height yoke 326 is a rectangular cuff interrupted in a mid-portion of a distal side to form locking left and right hands 352 respectively ride vertically in the left and right vertical rectangular slots 336. The locking left and right hands 352 have respective ridged proximal surfaces (not shown) that are selectively drawn proximally into locking engagement by a height locking lever 356 with a ridged surface 358 on a proximal side of each vertical rectangular slot 336. Lifting the height locking lever 356 unlocks the height yoke 326 for height adjustment. Proximal top surface of the height yoke 326 serves as a sight 360 to read a height measurement scale 362 presented on a proximal surface of the pedestal 328. Raising the height locking lever 356 takes the height yoke 326 out of locking engagement to the pedestal 328 as the height yoke 326 is vertically repositioned.

Symmetrical mounting provisions for the primary targeting rail 322 allows for use on either side of pedestal 328 so that full access may be made to the lateral fence 330. The attachment axle 324 allows rotation so that an axis of penetration may include an upward or downward trajectory. In the illustrative version proximal corners of the height yoke 326 includes angle detents 364 (e.g., −15°, 0°, +15°) that are selectable by an angle lock lever 366. The primary targeting rail 322 includes a distal detent 347 that serves as a home reference for a fiducial holder or monocle, examples of which are described herein but not shown in FIG. 5.

Figure 6:
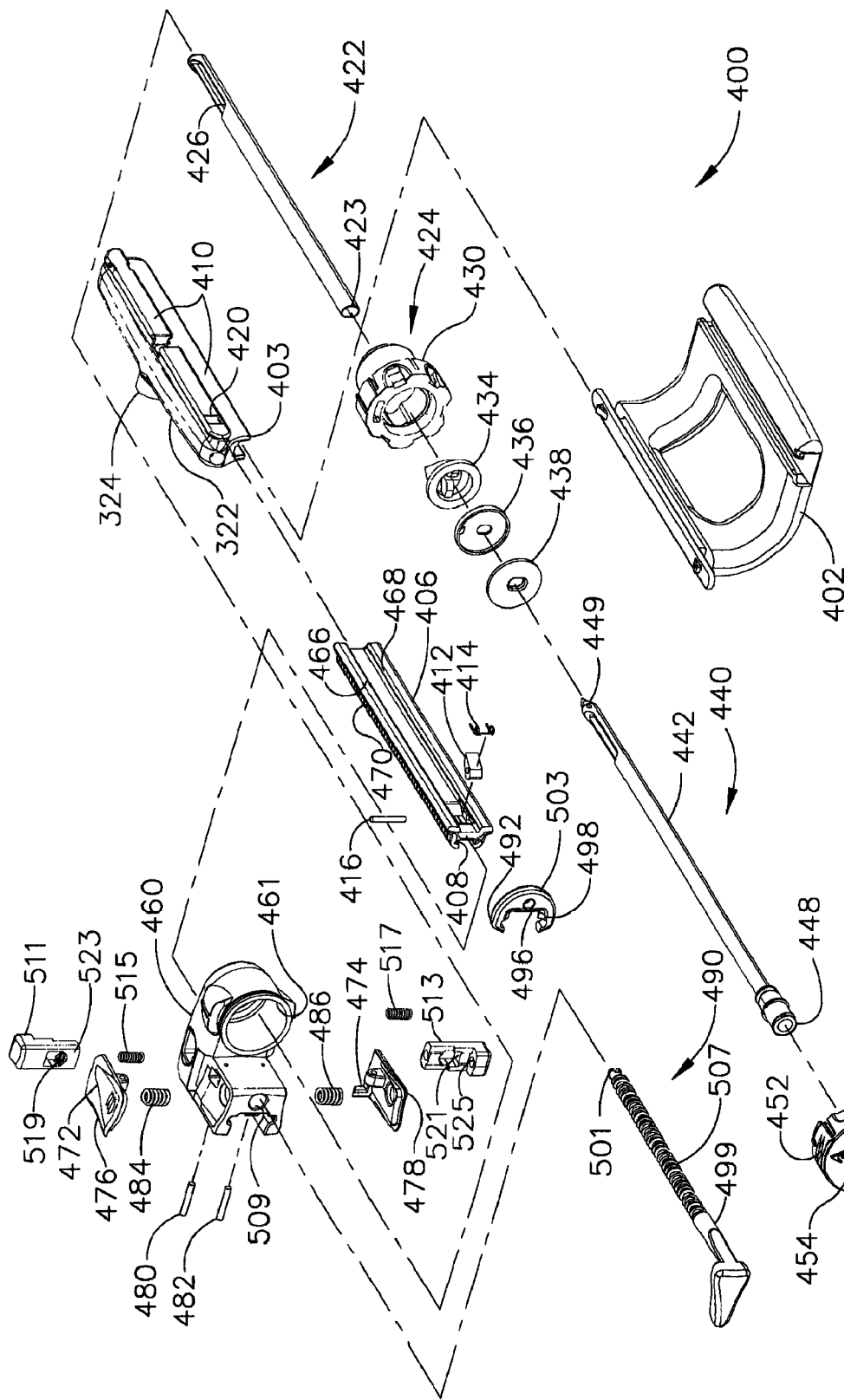
FIG. 6 is a disassembled perspective view of an alternative guidance system for the pedestal and targeting rail of FIG. 5.

In FIG. 6, a further alternative guidance assembly 400, that may be attached to the lateral fence supported pedestal 320 of FIG. 5, includes a cradle 402 that engages a bottom channel 403 of the primary targeting rail 322. To provide additional guidance to the MRI biopsy device 14 of FIGS. 1-3, a secondary targeting rail 406 includes a lateral channel 408 that is guided along a longitudinal guide tab 410 of the primary targeting rail 322. When fully engaged thereon, a pawl 412 pivoting under urging of a pawl spring 414 about a vertical pawl pin 416 in a lateral window 418 proximally positioned in the secondary targeting rail 406 drops into a proximal detent 420 proximally positioned on the primary targeting rail 322.

A sleeve 422 includes a hollow shaft (or cannula) 423 that is proximally attached to a cylindrical hub 424 and has a lateral aperture 426 proximate to an open distal end 428. The cylindrical hub 424 has an exteriorly presented thumbwheel 430 for rotating the lateral aperture 426. The cylindrical hub 424 has an interior recess 432 that encompasses a duckbill seal 434, wiper seal 436 and a seal retainer 438 to provide a fluid seal when the shaft 423 is empty and for sealing to an inserted introducer obturator 440.

The introducer obturator 440 advantageously incorporates a number of components with corresponding features. A hollow shaft 442 includes a fluid lumen 444 that communicates between an imagable side notch 446 and a proximal port 448. The hollow shaft 442 is longitudinally sized to extend when fully engaging a piercing tip 449 out of the distal end 428 of the sleeve 422. An obturator thumbwheel cap 450 encompasses the proximal port 448 and includes a locking feature 452, which includes a visible angle indicator 454, that engages the sleeve thumbwheel 430 to ensure that the imagable side notch 446 is registered to the lateral aperture 426 in the sleeve 422. An obturator seal cap 456 may be engaged proximally into the obturator thumbwheel cap 450 to close the fluid lumen 444. The obturator seal cap 456 includes a locking feature 458 that includes a visible angle indicator 460 that corresponds with the visible angle indicator 454 on the obturator thumbwheel cap 430.

In FIGS. 7-11, the introducer obturator 440 is shown in greater detail. The obturator 440 has the hollow shaft 442 that provides the multi-function fluid lumen 444. In FIG. 8, the piercing tip 449 is formed by a flat blade 441 that is attached within a vertical slot 445 formed between two distal ramped triangular supports 447, 449. The proximal port 448 of the hollow shaft 442 forms a hose nib (e.g., leur fitting) for using the lumen 444 for pneumatic or fluid transfers to the imagable side notch 446, which serves as an imagable side notch and is proximate to the flat blade 441. In FIGS. 7, 9, exterior engagement features on the proximal port 448 include a circumferential raised ring 451 proximal to a circumferential ring slot 453. In FIG. 9, a vent hole 455 through an opposite lateral side to the imagable side notch 446 allows equalization of pressure within a sleeve or the use of a vacuum lumen in the sleeve (not shown in FIGS. 7-11). In FIGS. 10, 11, a top guide slot 457 passes longitudinally down the proximal port 448 of the hollow shaft 442 so that engagement with a sleeve may be keyed to align the imagable side notch 446 with a side aperture in the sleeve. In FIGS. 7, 9, rounded leading and trailing edges 459, 461 of the imagable side notch 446 minimize tissue trauma. Alternatively, the top guide slot 457 may allow visual indexing so that confirmation may be confirmed that the imagable side notch 446 is rotated out of alignment with a side aperture during penetration to prevent tissue entering the image side notch 446. Thereafter, the imagable side notch 446 may be rotated into alignment for imaging confirmation and/or use of the multi-function lumen 444.

It should be appreciated that various other sleeve, obturator, stylet and/or probes may advantageously be used, such as described in the U.S. nonprovisional patent application entitled LOCALIZATION MECHANISM FOR AN MRI COMPATIBLE BIOPSY DEVICE to Hibner et al., Ser. No. 10/171,330, filed on 23 Apr. 2002, and published on 23 Oct. 2003 as Pub. No. US 2003/0199785, and the U.S. nonprovisional patent application filed on even day herewith entitled "MRI BIOPSY APPARATUS INCORPORATING A SLEEVE AND MULTI-FUNCTION OBTURATOR" to Tsonton et al, Ser. No. 11/103,718, the disclosures of both of which are hereby incorporated by reference in their entirety.

Figure 12:
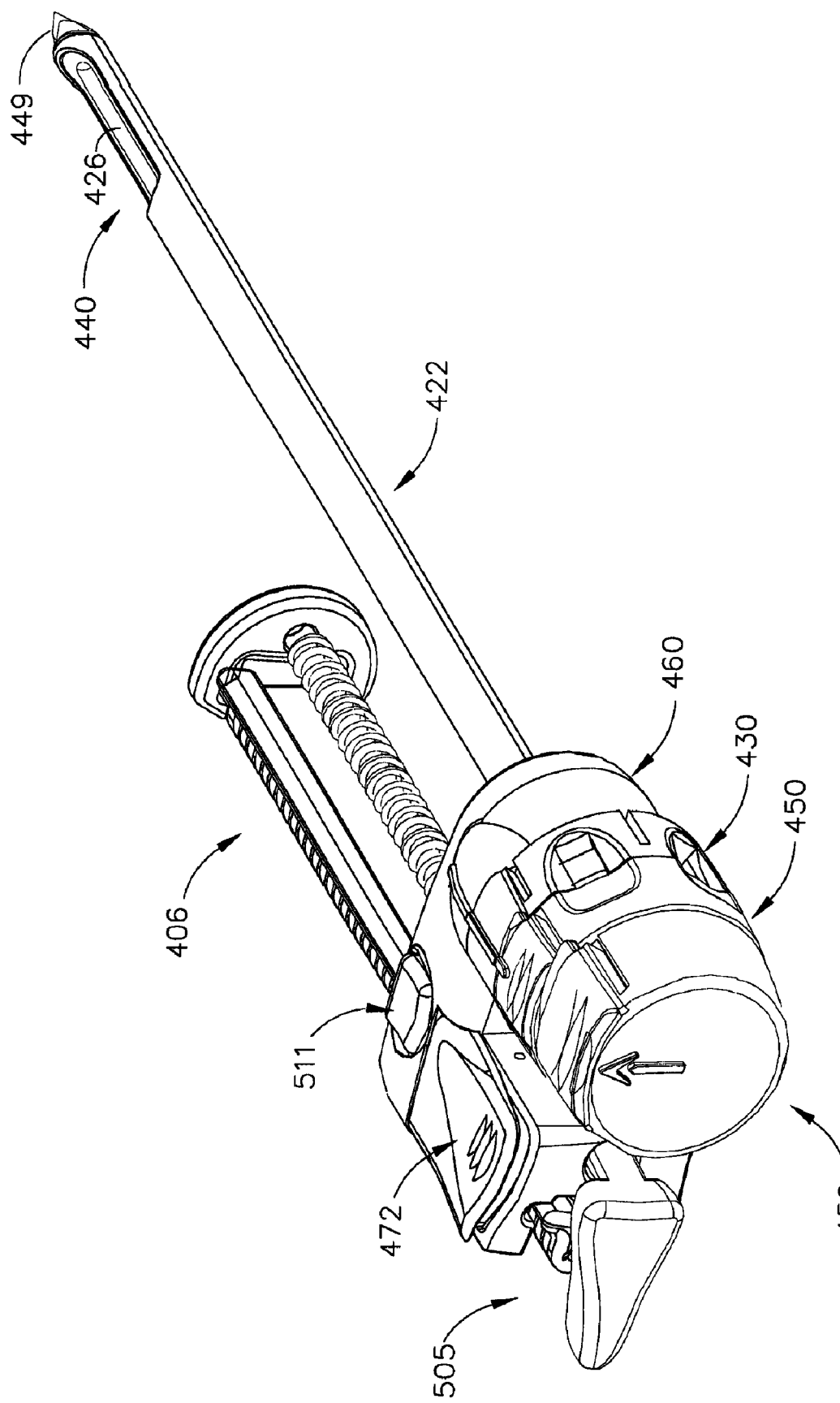
FIG. 12 is a perspective view of the alternative secondary targeting rail, sleeve and obturator of the guidance system of FIG. 6.

With reference to FIGS. 6 and 12, the sleeve 422 is guided during penetration of tissue by a sleeve mount 460 having a sleeve hub 462 that receives the cylindrical hub 424 of the sleeve 422. The sleeve mount 460 has a lateral sleeve hub channel 464 that slides along top and bottom guide flanges 466, 468 of the secondary targeting rail 406, each having an aligned and recess ridged, ratcheting surface 470 that interacts with a respective top and bottom ratcheting feature 472, 474 on respective top and bottom rail lock rocker latches 476, 478 that are engaged by respective top and bottom latch pins 480, 482 in respective sides of the sleeve mount 460. The ratcheting features 472, 474 are proximally ramped such as to allow distal movement. Distal portions of each rail lock rocker latches 478, 480 are biased away from the sleeve mount 460 by respective rail lock compression springs 484, 486 to bias the ratcheting features 472, 474 into contact with the ridges surfaces 470 of the guide flanges 466, 468. Simultaneous depression of the rail lock rocker latches 476, 478 allow the sleeve mount 460 to be drawn proximally, withdrawing any sleeve 422 supported therein, until the sleeve mount 460 reaches a proximal end of the secondary targeting rail 406, whereupon the sleeve mount 460 rotates the pawl 412 clockwise (as viewed from the top) and is thus engaged to the secondary targeting rail 406 as the secondary targeting rail 406 is unlocked from the primary targeting rail 322 causing removal therefrom with continued proximal movement.

Before mounting the secondary targeting rail 406 onto the primary targeting rail 322 in the first place, the sleeve mount 460 is advantageously adjustably positioned on the secondary targeting rail 406 to set a desired depth of penetration. In particular, a depth guide 490 is formed by a crescent-shaped depth indicator 492 having a lateral channel 496 shaped to engage the top and bottom guide flanges 466, 468. Forward ramped surfaces 498 on the top and bottom of the lateral channel 496 are positioned to engage the ridged ratcheting surfaces 470 on the secondary targeting rail 406 allowing assembly by inserting the depth indicator 492 from a distal end of the secondary targeting rail 406. Frictional engagement thereafter resists further proximal movement and strongly opposes any distal movement, especially from a depth lead screw 499 of the depth guide 490 whose distal end 501 rotates within an outboard hole 503 in the depth indicator 492 and whose proximal end deflects laterally as a depth actuator lever 505 used to rotate and longitudinally position the depth lead screw 499 therein. A mid portion of the depth lead screw 499 is received in a longitudinal through hole 509 formed in the sleeve mount 460 outboard to its lateral channel 408. For coarse depth adjustment, outer lead threads 507 on the depth lead screw 499 selectively engage the sleeve mount 460 until top and bottom coarse ("quick") adjust buttons 511, 513 are inwardly depressed into the sleeve mount 460, compressing respective top and bottom coarse adjust compression springs 515, 517. Each coarse adjust button 511, 513 includes a respective vertically elongate aperture 519, 521 whose inward surface presents a worm gear segment 523, 525 to engage the outer lead threads 507 on the depth lead screw 499 when urged into engagement by relaxed coarse adjust compression springs 515, 517.

In FIG. 13, a localization fixture 502 for use with the breast coil 18 of FIG. 1 advantageously includes a base assembly 504 having a top recess 506 sized to receive a detachable lateral assembly (precision tray) 508 that contains a pedestal 510 that slides when a cam-type lock 512 is released within a horizontal window 514 defined in the detachable lateral assembly 508. The pedestal 510 in turn defines a vertical window 516 within which a y-axis mount 518 slides up and down with a cam-type lock 519 to vertically (y-axis) position a z-axis track 520 with folding front mount monocle 522.

In FIGS. 13-14, it should be appreciated that the folding front mount monocle 522 is advantageously placed near to the lateral window 92. Thus, even if the z-stop (not shown) is positioned proximally or not used, a reference point is provided near to the patient's breast for marking and scoring. In addition, the monocle 522 may be rotated away so as to not interfere with other components.

The base assembly 504 includes downwardly open left and right channels 524, 526 that engage features on an underlying medial plate (not shown) that may be disengaged by left and right side levers 528, 530. An open track 532, defined in the top recess 506, receives one or more downwardly projecting features (not shown) from the detachable lateral assembly 508 for engagement to the track 532. Once fully positioned, these features would engage the track 532 to provide a tactile confirmation to a clinician that the detachable lateral assembly 508 is fully inserted. A push button 534 proximally positioned to the detachable lateral assembly 508 allows disengagement. It is advantageous in many instances that the engagement and disengagement of the various components of the localization fixture 502 provide positive tactile and visual confirmation that assembly and engagement has been achieved while producing a minimum of noise that may be disconcerting to a patient.

An advantage afforded by the detachable lateral assembly 508 is that a clinician may preset the desired coordinates for sleeve/probe insertion without the inconvenience of making these settings at the MRI machine. In particular, the pedestal 512 and z-axis track 520 may be adjusted within their respective windows 514, 516 and locked into place. A z-stop (not shown) may similarly be positioned accurately upon the z-axis track 520.

Figure 15:
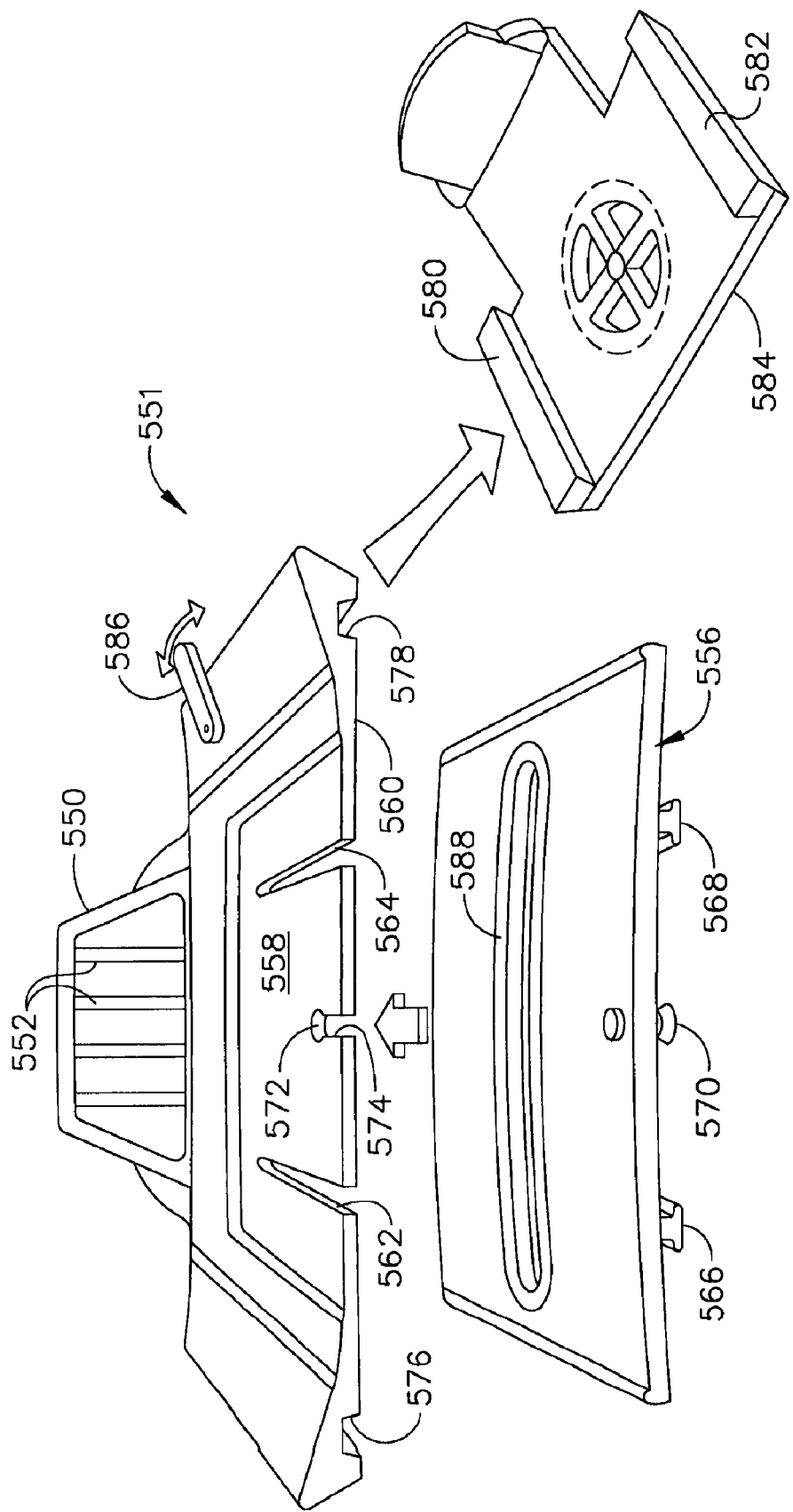
FIG. 15 is a perspective view of a localization fixture for the MRI biopsy system of FIG. 1.
Figure 16:
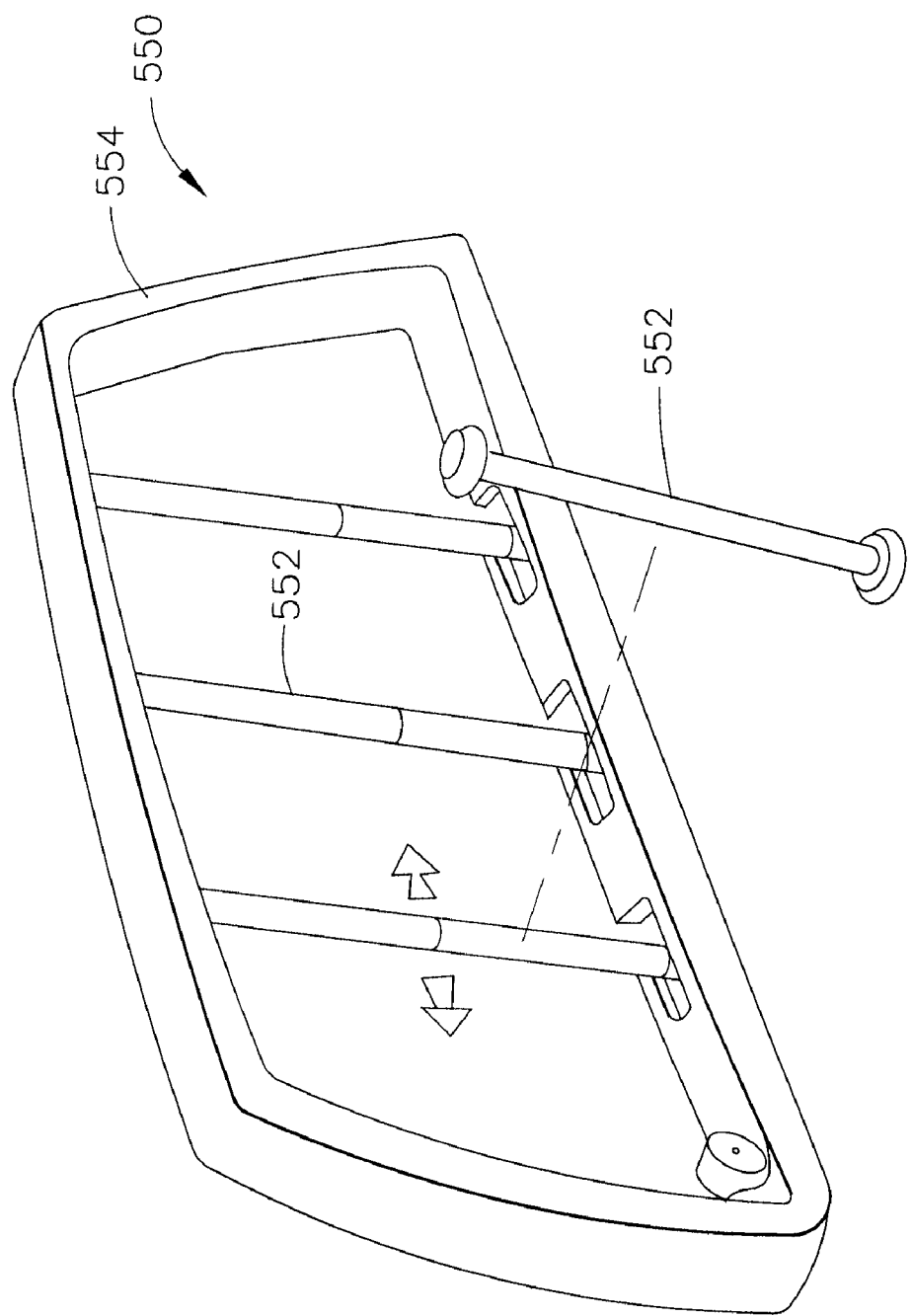
FIG. 16 is a perspective view of a lateral plate having displaceable and/or removable bars for the localization fixture of FIG. 33.

In FIGS. 15-16, an alternative lateral plate 550 for a localization fixture 551 advantageously includes positionable and/or removable bars 552. It should be appreciated that the bars 552 are illustrated as being vertically assembled to a frame 554 but may alternatively be horizontally assembled in some applications. By being able to offset or remove any given bar 552, an inconvenient situation of having a desired insertion point being behind a bar 552 is avoided.

In FIG. 16, the localization fixture 551 advantageously allows a significant amount of adjustment to be accomplished so that localization and guidance components may be centered around the patient's breast, rather than centering the patient's breast within a device. In particular, a precision tray 556 is provided that is guided into position on a top recess 558 of a base assembly 560 by a pair of left and right open tracks 562, 564 therein that engage left and right downwardly projecting T-shaped features 566, 568. A click stop 570 snaps into a distal aperture 572 of a center track 574.

The base assembly 560 in turn has downwardly open left and right dovetail channels 576, 578 that slidingly engage upwardly extending dovetail rails 580, 582 of a medial plate 584. A cam lock 586 on the base assembly 560 causes the dovetail rails 580, 582 to be locked in respective dovetail channels 576, 578.

Figure 17:
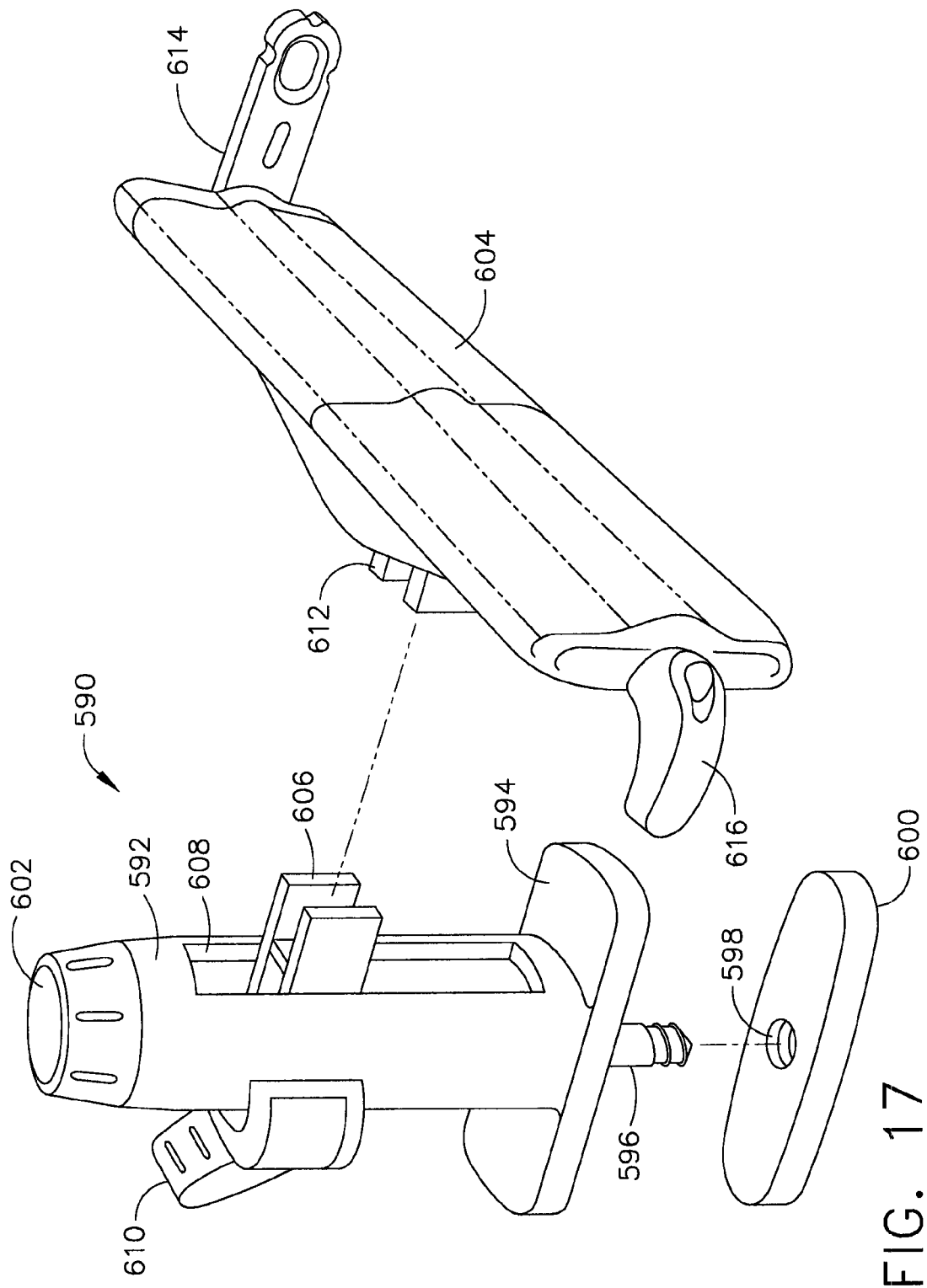
FIG. 17 is a perspective view of a tower pedestal for the localization fixture of FIG. 15.

In FIG. 15, a narrow lateral channel 588 across the precision tray 556 defines lateral (x-axis) positioning for a tower pedestal 590, which is depicted in FIG. 34. In FIG. 17, the tower pedestal 590 includes a pedestal body 592 with a base 594 sufficiently wide to span across the narrow lateral channel 588. A threaded post 596 downwardly extends through the narrow lateral channel 588 to engage a threaded hole 598 in a lock down member 600 that slides along an undersurface of the precision tray 556. Selective engagement of the tower pedestal 590 is achieved by rotating a lock down knob 602 on the top of the pedestal body 592, which rotates the threaded post 596 to space apart or clamp the base 594 and lock down member 600.

Vertical (y-axis) positioning of a molded z-axis rail 604 is provided by a male friction member 606 that is constrained within a vertical channel 608 in the pedestal body 592 and is clamped by a cam lock 610. The z-axis rail 604 includes a female friction clamp 612 to engage the male friction member 606. A monocle mount 614 is pivotally attached to a distal end of the z-axis rail 604 and is remotely pivoted by a proximal monocle flip lever 616 on a proximal end of the z-axis rail 604.

Figure 18:
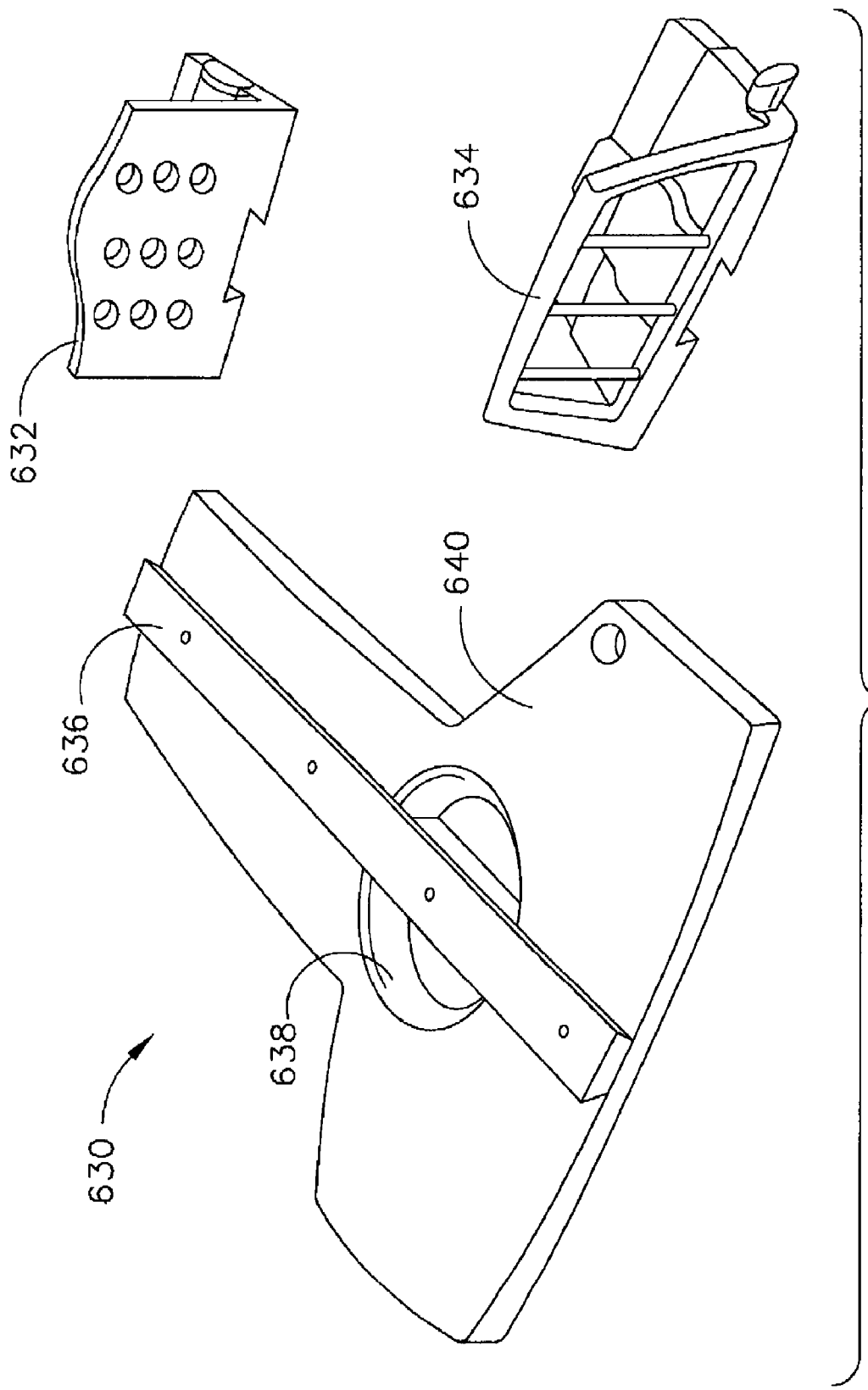
FIG. 18 is a perspective view of a breast localizing portion of a one-rail localization fixture.

In FIG. 18, breast localizing portions of a one-rail localization fixture 630 are depicted that advantageously allow a single datum to enhance accuracy. All tightening to lock rear fence 632 and front fence 634 occurs in the same direction against a common surface of a rail 636 that is mounted over a molded-in coil mount 638 of a base plate 640. A lateral assembly (not shown) would advantageously engage and lock to the same rail 636.

Figure 19:
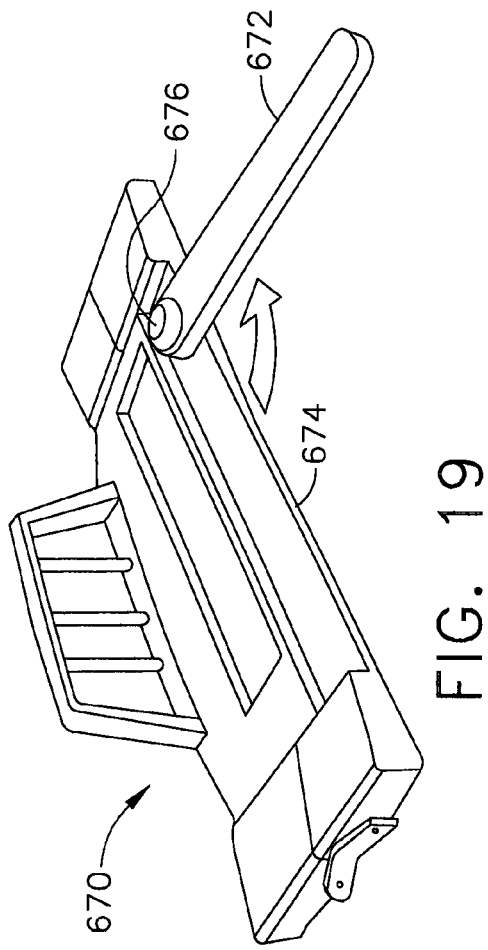
FIG. 19 is a perspective view of a localization fixture incorporating an equipment protection flip-out lever for the MRI biopsy system of FIG. 1.

The localization and guidance features described herein provide a great deal of accuracy. It would be further desirable to avoid inadvertent contact to these portions that cause, for instance, an inserted sleeve or probe to be displaced. In particular, with an MRI biopsy device mounted to a localization fixture, a clinician may inadvertently bump into the proximally extending holster, overcoming the locking of the guidance components. To that end, in FIG. 19, a localization fixture 670 may advantageously incorporate a manually or spring-opened lever 672 that extends proximally from a main base 674. A spring-loaded pop-up lock 676 engages when the lever 672 is fully extended.

Figure 20:
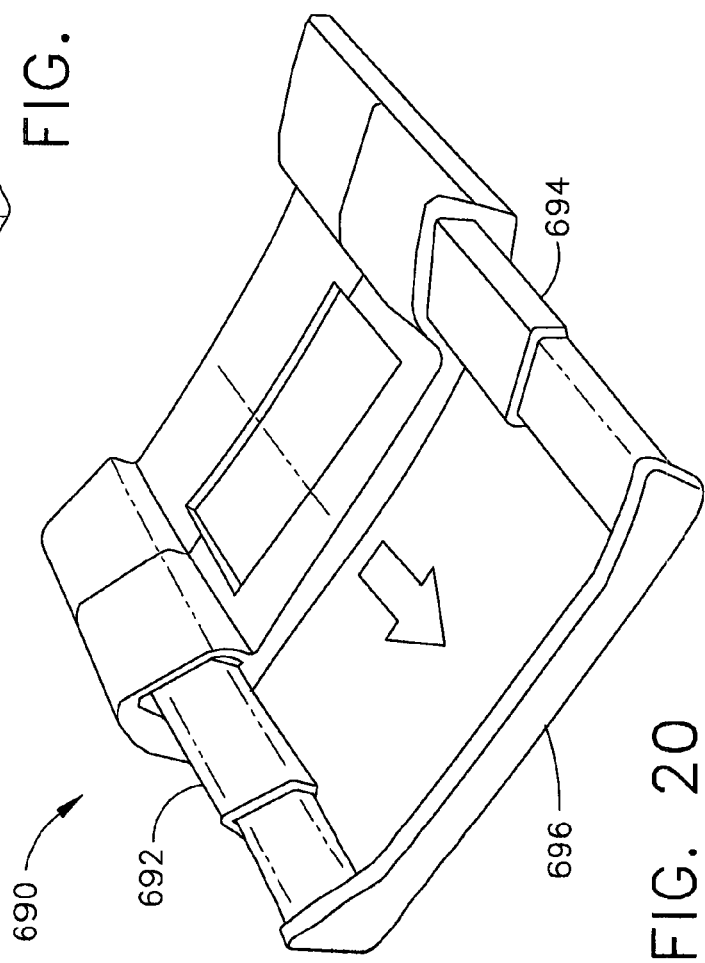
FIG. 20 is a perspective view of a localization fixture incorporating a telescoping equipment protector for the MRI biopsy system of FIG. 1.

Alternatively, in FIG. 20, a localization fixture 690 includes left and right telescoping arms 692, 694 distally connected by a bar 696 that are manually, compressed-gas, or spring-biased to extend outwardly.

In FIGS. 21-24, a localization fixture 700 advantageously facilitates centering the patient breast between a rear fence 702 and lateral plate 704 while creating an even pressure to avoid discomfort, eliminating the need to reach under the patient to adjust a medial plate 706 that supports the rear fence 702, creating a two-step sequential lock down mechanism. In particular, the locks are positive to provide tactile and visual feedback to the clinician but are noiseless for patient comfort. Keeping the patient comfortable has a benefit of making her less likely to move. In particular, the flexible, disposable rear fence 702 is centrally supported at 709, allowing its lateral portions 708, 710 to flex to the patient's needs. The lateral plate 704 is curved to also enhance comfort and to assist in centering the breast. A cam lock 701 cams against a right proximal portion 730b of a right guide surface 728b to thereby urge the lateral plate 704 into locking engagement with a corner surface 703 (FIG. 40) of a left proximal portion 730a of a left guide surface 728 of a supporting base plate 705 of the localization fixture 700. Left and right distal portion 732 respectively of the left and right guide surfaces 728a, 728b of the base plate 705 guides the medial plate 706. In particular, resilient guide members 733, 734 extend laterally from the medial plate 706 for centering respectively against distal portions 732a, 732b.

Figure 23:
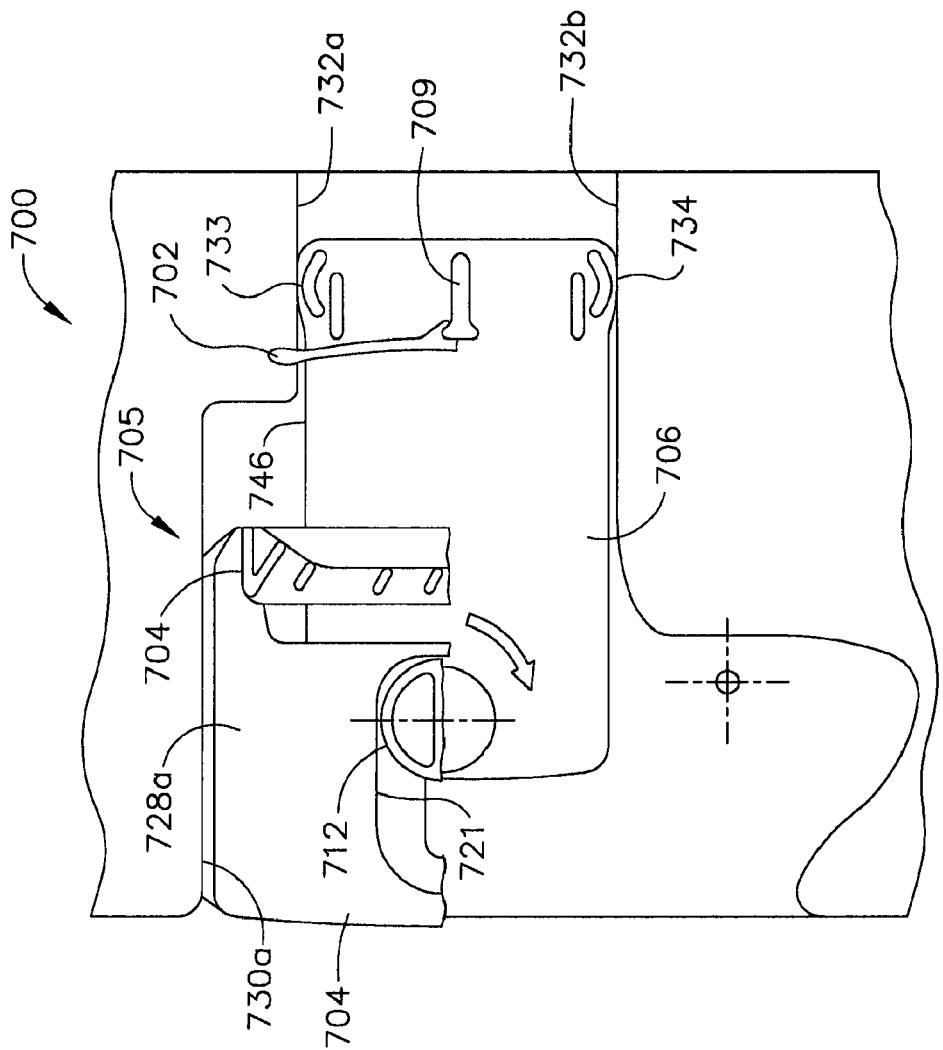
FIG. 23 is a top view of a localization fixture partially cut away for the MRI biopsy system of FIG. 1, including a lateral plate having flexible ribbing.
Figure 24:
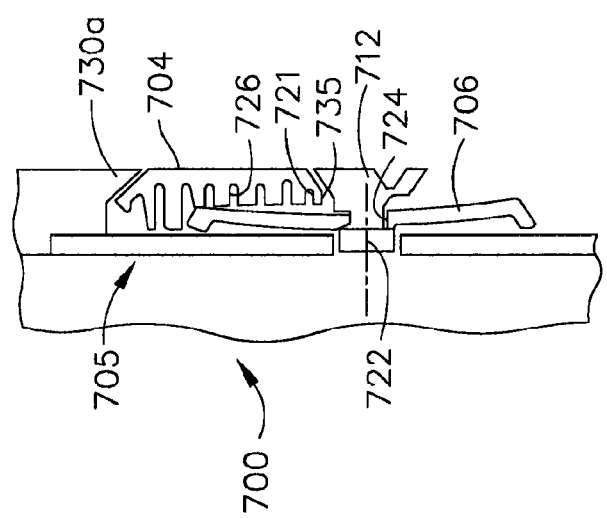
FIG. 24 is a front cross sectional view in elevation of the lateral plate and top recess of the lateral plate and medial plate of FIG. 21 taken along lines 24-24.

In FIGS. 23-24, a circular lock control 712 includes a control knob 720 which rotates 90° within a knob recess 721 formed in the lateral plate 704 communicating via a shaft 722 to a sliding member 723 that slides within a slot 724 the medial plate 706 by including camming surfaces 735 of the knob 720 that force downwardly projecting ribbing 726 of the lateral plate 704 into contact with the medial plate 706 for stabilization and accuracy. Insofar as these plates 704, 706 are not required to accurately position instruments, this flexibility is satisfactory. These two controls 712, 701 advantageously lock into position the plates 704, 706 that thus compress and localize the patient's breast without having to reach under the patient.

Figure 25:
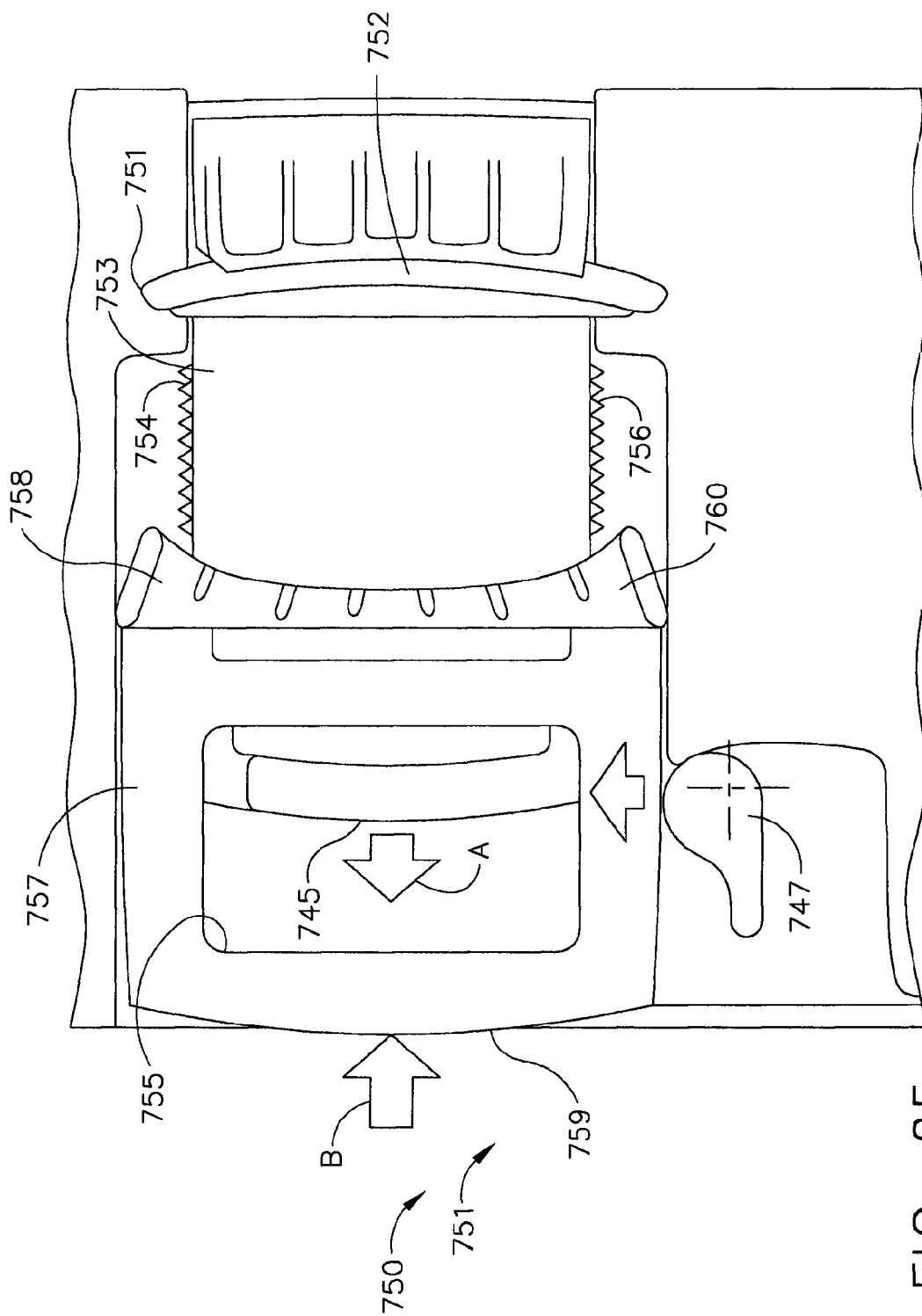
FIG. 25 is a top view of a localization fixture having a squeeze trigger with a cam lock for medial fence adjustment.

In FIG. 25, a localization fixture 750 advantageously includes a disposable flexible and curved medial pad 752 formed of a material known for use in prosthetic devices due to its flexibility for low pressures and its ability to be quickly warmed for comfort mounted to a medial fence 751 and medial plate 753. Accordion-like vertical bars 754, 756 contact the top and bottom of the patient's breast to assist in providing equal compression about the patient's breast. Thickened lateral edges 758 of a lateral fence 760 increase strength and stability. Proximal controls advantageously include a palm rest 759 extending from a lateral plate 757 presenting an aperture 755 for the fingers of the user to wrap around a medial grip 745 that is attached to the median plate 753, allowing a convenient hand squeeze control 751 to draw the lateral fence 760 toward the medial fence 751 to compress the patient's breast whereupon the user uses his free hand to actuate a cam lock 747 to lock the lateral and median plates 757, 753 together.

Figure 26:
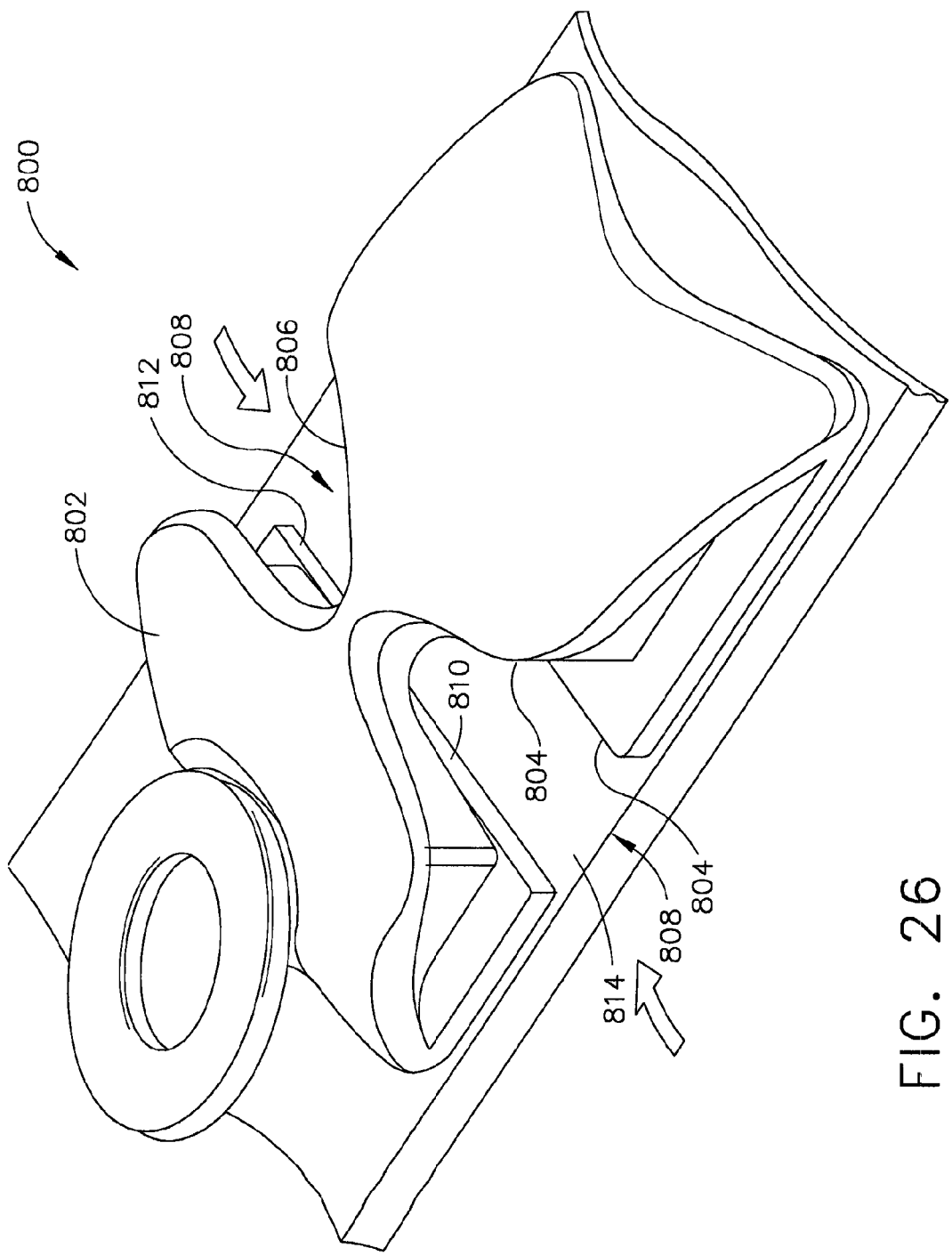
FIG. 26 is a perspective view of an alternative patient support for the MRI biopsy system of FIG. 1.

In FIG. 26, an alternative patient support 800 similar to massage tables for full support incorporates an hour-glass shaped arched upper portion 802 with left and right lateral cutouts 804, 806 to allow the patient's breast to hang pendulously for the localization fixture (not shown in FIG. 26). Below and connecting to the top and bottom of the upper portion 802 is a guide surface 808 having corresponding left and right lateral cutouts 810, 812, exposing a table surface 814 that becomes the y-axis reference.

Figures 27, 28:
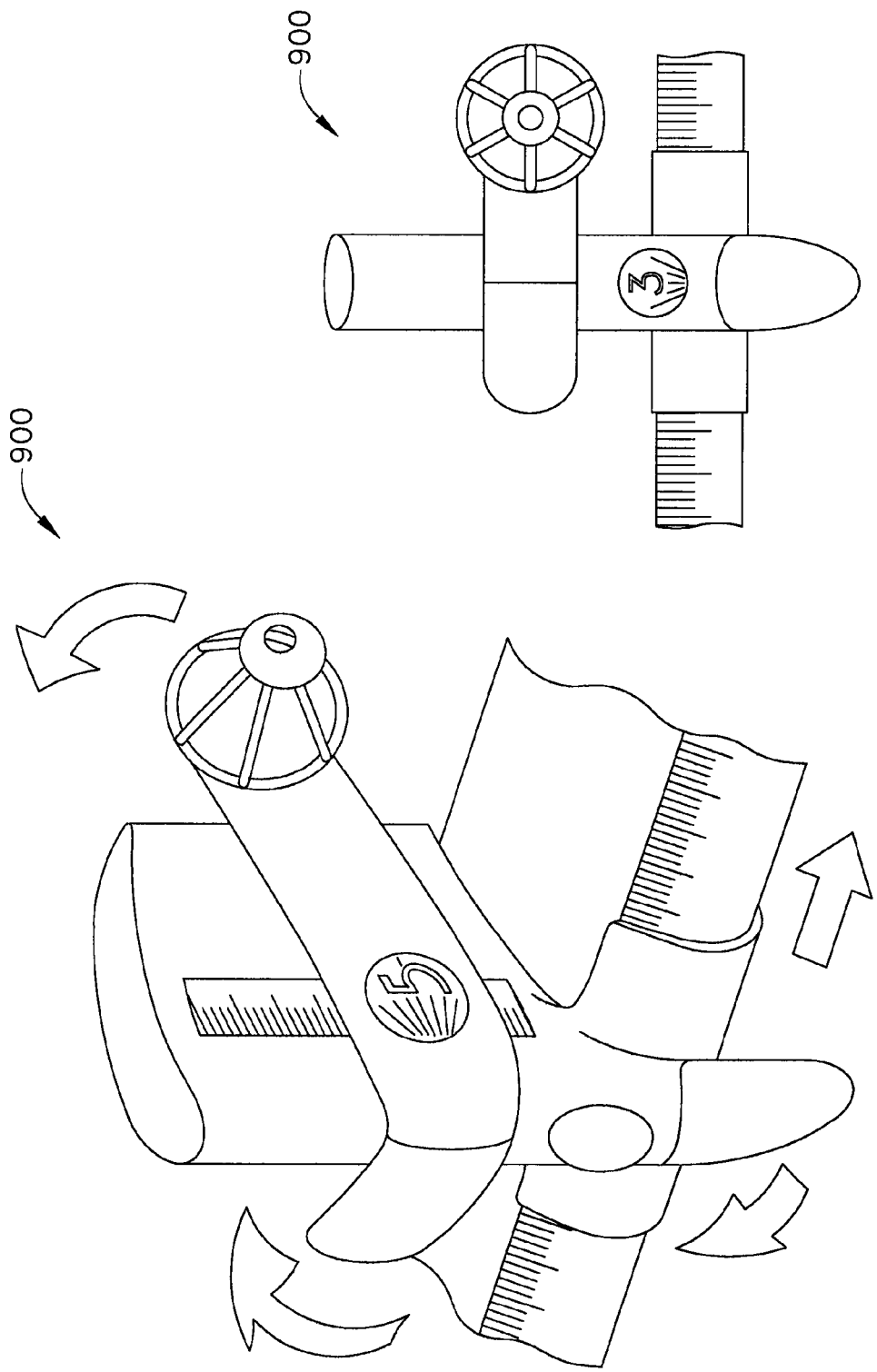
FIG. 27 is a perspective view of guidance components having tablesaw style guides and locking levers of a localization fixture for the MRI biopsy system of FIG. 1.
FIG. 28 is a side view in elevation of the guidance components of FIG. 27.

In FIGS. 27-28, guidance components of a localization fixture 900 advantageously incorporate slides, locks and magnifying bubble gauges reminiscent of carpentry table saws for having everything outside on the outer edges of the device, enhancing visibility of measurements. Locking levers are semantically obvious with respect to position. A large cross sectional area of a lower rail provides superior support.

Figure 30:
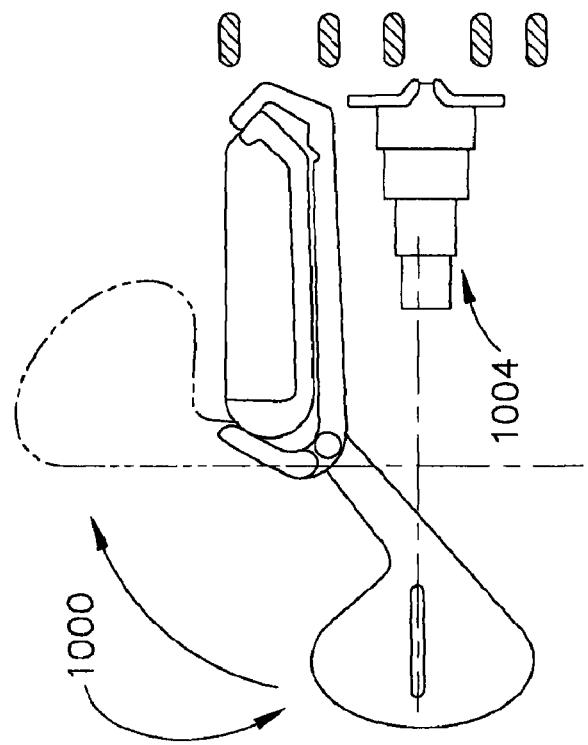
FIG. 30 is a top cross sectional view of the guidance components of FIG. 29.
Figure 29:
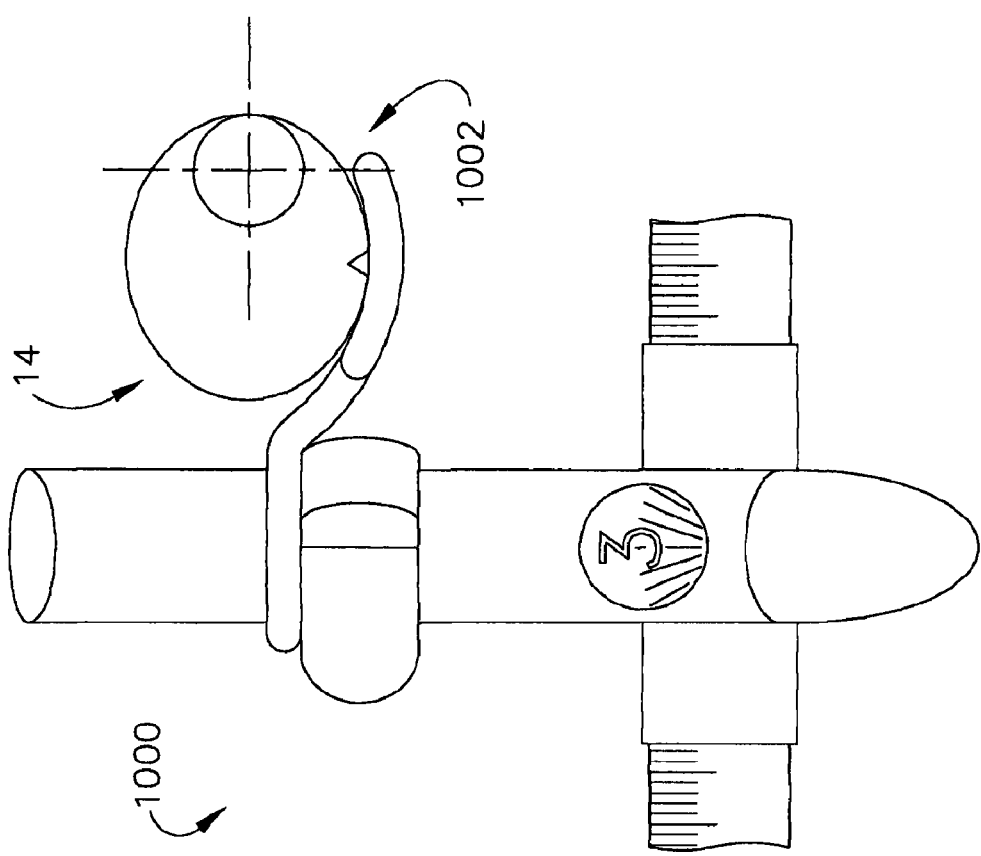
FIG. 29 is a front view in elevation of guidance components of a localization fixture for the MRI biopsy system of FIG. 1 having a separate support arm and distal targeting ring.

In FIG. 29, guidance components of a localization fixture 1000 advantageously separate targeting and support for a distal end of an MRI biopsy device 14 with a proximal support arm 1002, that may be rotated out of the way when the MRI biopsy device 14 is not present, as shown in FIG. 30. The proximal support arm 1002 supports the weight of the MRI biopsy device 14 and has a secondary locking mechanism for accurate and secure positioning (not shown). A distal end (i.e., probe) of the MRI biopsy device 14 is supported and aligned by a separate structure, illustrated by a telescoping targeting ring 1004, and is depicted in FIG. 30.

In FIG. 31, an X-Y alignment fixture 1006 is depicted as an approach to aligning telescoping targeting ring 1004. A base plate 1008 of the localization fixture 1000 includes a lateral channel 1009 that guides a horizontal support 1010 of the X-Y alignment fixture 1006. Scale marks (not shown) may be read from a scale window 1012 with a locking mechanism (not shown) to maintain this lateral (X) position. A vertical guide 1014 (FIG. 31) of the X-Y alignment fixture 1006 may be advantageously formed of transparent material and placed proximate to a lateral plate 1016. This vertical guide 1014 is also advantageously hinged to the horizontal support 1010 such that it may be flipped down when desired. The vertical guide 1014 includes a vertical slot 1018 centered within a vertical channel 1020. A distal end of the telescoping targeting ring 1004 includes locking cam ridges 1022 that may be brought into engagement with the vertical channel 1020 to lock the telescoping targeting ring 1004 at a selected vertical (Y) position. This adjustment may be performed prior to assembling this portion of components to the MRI breast coil (not shown in FIGS. 31-33). In FIGS. 31-33, the telescoping targeting ring 1004 is shown to have a septum 1024 that is pierced by a sleeve or probe, which assists in preventing inadvertent retraction and the forming of a pneumatic seal. The telescoping targeting ring 1004 also includes a side port 1026 that may be used for a drain and other purposes.

In FIGS. 34-36, a guide rail member 1100 of a localization fixture 1102 is depicted that has enhanced strength, button actuated needle rotation and an enhanced sample collection window. Cam ridges 1104 of a probe-to-rail interface 1106 increase the registration surface area to improve support and strength. A button 1108 that mechanically communicates through a rotation mechanism 1110 allows remote rotation (e.g., 10 degrees per actuation), obviating the need to reach in and manually rotate. A sample collection window formed of transparent material enhances visibility.

Figure 38:
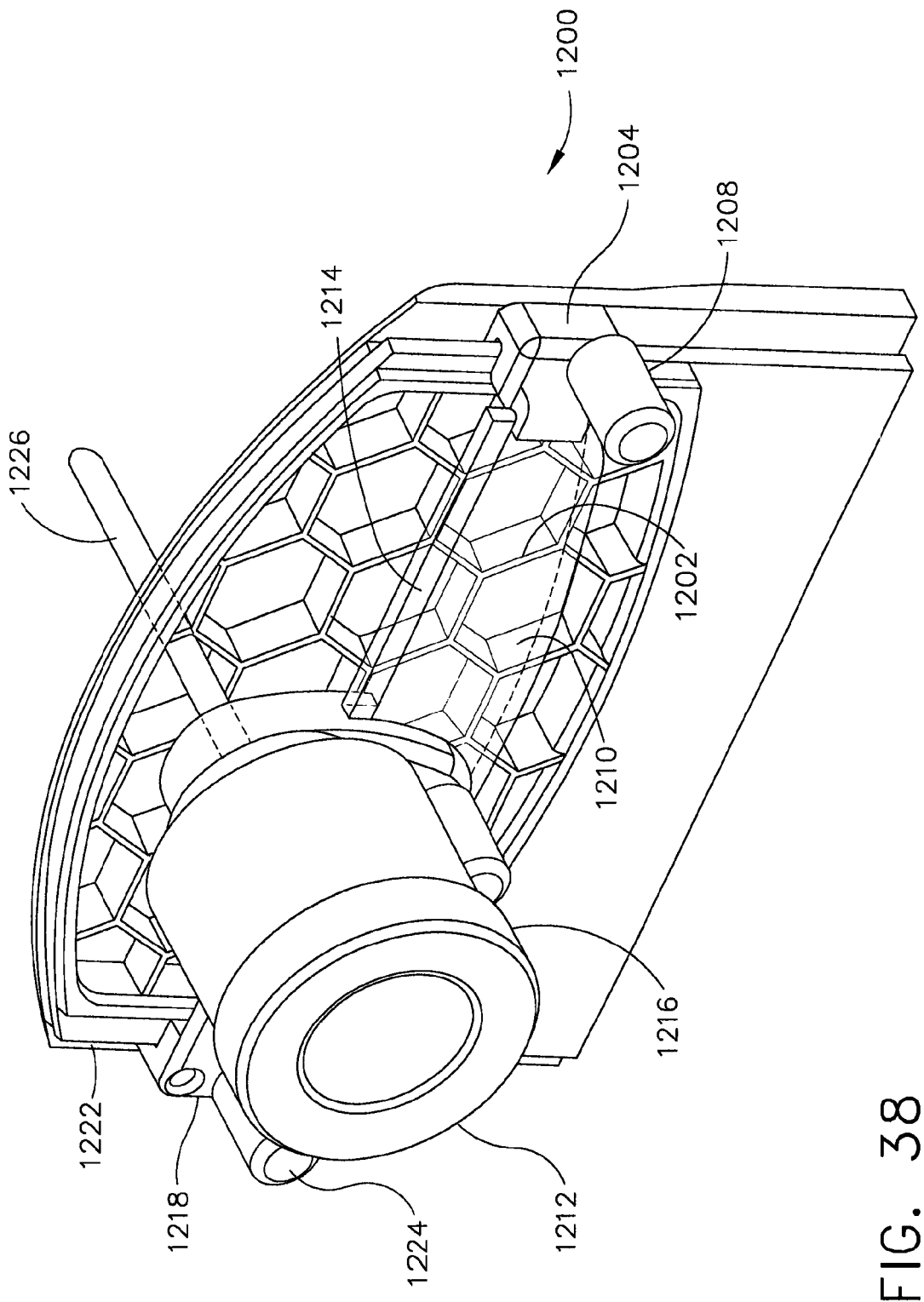
FIG. 38 is a perspective view of the honeycomb lateral plate with the integral distal targeting fixture of FIG. 37, shown in its swung closed position with a probe guide installed.

In FIGS. 37-38, a honeycomb lateral plate 1200 with an integral distal targeting fixture 1202 may be used with one of the afore-mentioned localization fixtures (not shown in FIGS. 37-38). The integral distal targeting fixture 1202 includes a vertically sliding, door hinged attachment 1204 to a right-side channel 1206 of the lateral plate 1202. A right adjustment screw 1208 locks the vertically sliding, door hinged attachment 1204 to a particular vertical (Y) coordinate. A horizontal arm 1210 of the integral distal targeting fixture 1202 includes a reticule 1212 that is horizontally slidingly engaged to a top track 1214 and locks at a selected lateral (X) location by a middle locking screw 1216. At a leftmost end of the horizontal arm 1210, a latching mechanism 1218 is formed by grooved end 1220 that engages a left-side vertical channel 1222 of the lateral plate 1200 that is held in position by a left locking screw 1224, as shown in FIG. 38, which also shows a sleeve 1226 and obturator 1228 inserted through the reticule 1212 to interface with an MRI biopsy device (not shown in FIGS. 54-56).

Figure 39:
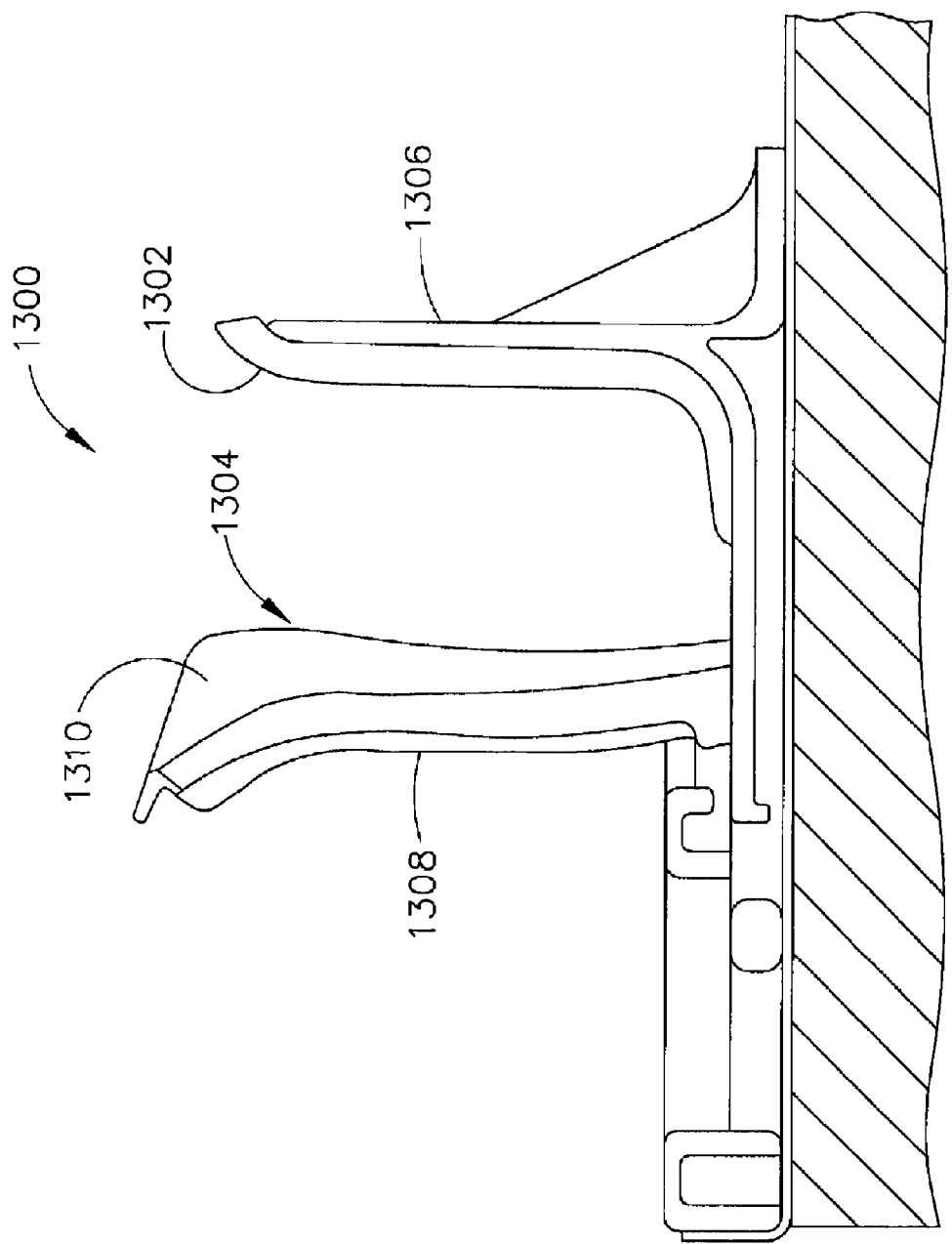
FIG. 39 is a side view in elevation of a medial plate and medial fence and a lateral plate of a localization fixture that incorporates soft elastomeric pads to enhance support and comfort.

In FIG. 39, a localization fixture 1300 advantageously includes shaped, soft, medial and lateral elastomeric pads 1302, 1304 (e.g., disposable gel) inwardly projecting respectively from a medial fence 1306 and lateral plate 1308. Thereby, conformability and patient comfort are enhanced. Increased posterior flexibility is anatomically correct, improving support. A top portion of the lateral plate 1308 advantageously tips outwardly, relying upon a thicker portion 1310 of the lateral elastomeric pad 1304 for patient support, which helps accommodate a more diverse population of patients.

Figure 40:
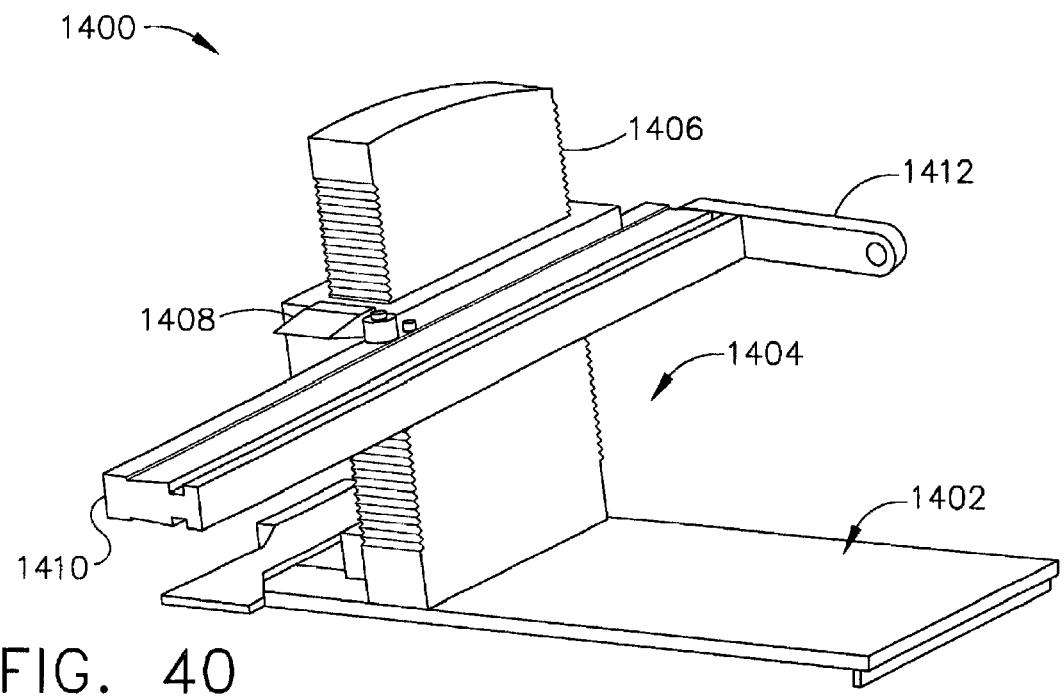
FIGS. 40-41 are perspective views of a ratcheting jack-style lock on an alternative pedestal for a localization fixture.
Figure 41:
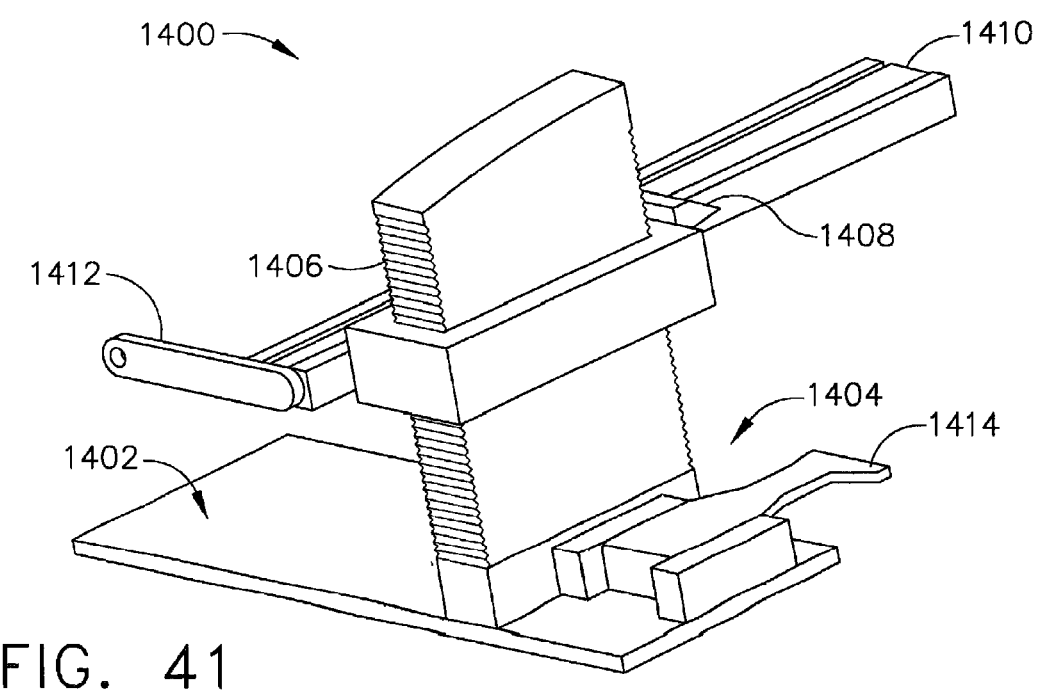

In FIGS. 40-41, a tower pedestal 1400 on a lateral plate 1402 forms a lateral assembly 1404 and includes ratcheting jack style ridges 1406 and a minor axis locking lever 1408 along a minor axis (vertical, Y) to position a hinged z-axis guide rail 1410, which is hinged at its proximal end to a cuff 1412 that encompasses the tower pedestal 1400. Thus, a monocle 1412 at a distal end of the guide rail 1410 may be rotated up out of the way when desired while maintaining a set Y-coordinate. Similarly, the lateral plate 1402 incorporates a major axis cam lock 1414 that is attached to the tower pedestal 1400 for locking at a particular lateral point (X).

Figure 42:
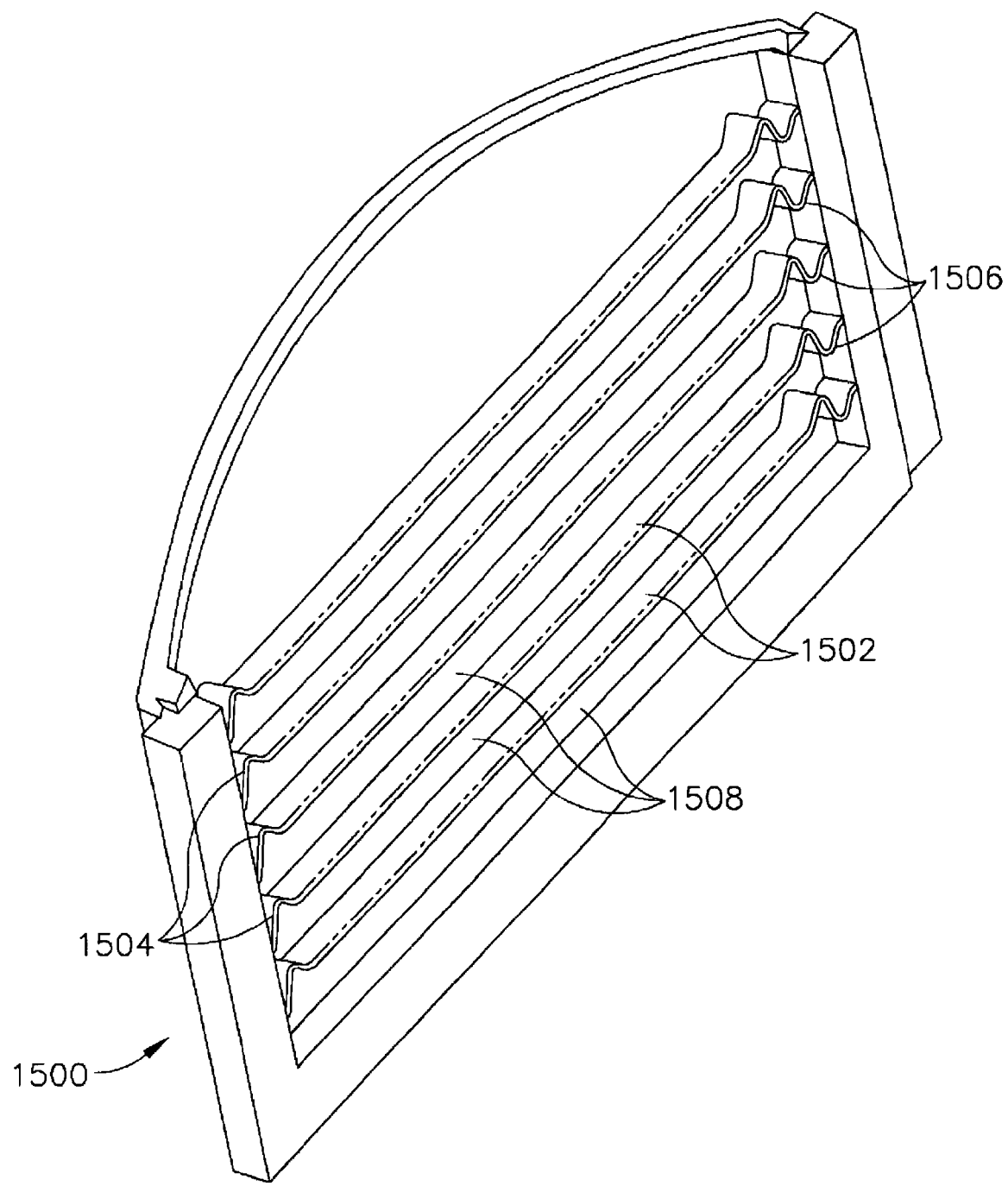
FIG. 42 is a perspective view of a lateral plate having displaceable grid members.
Figure 43:
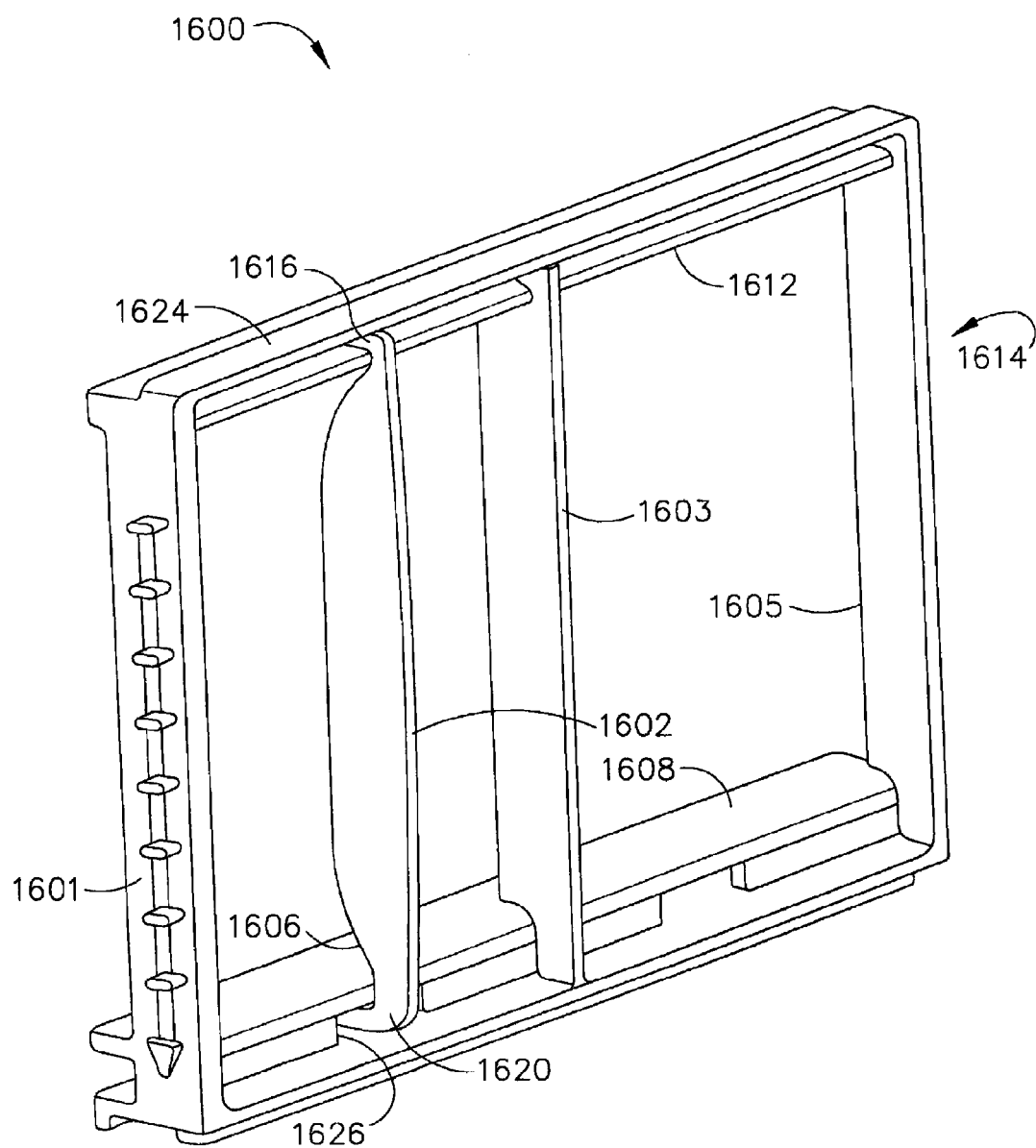
FIG. 43 is a front perspective view of a further alternative lateral fence having detachable bars for the MRI biopsy system of FIG. 1.
Figure 47:
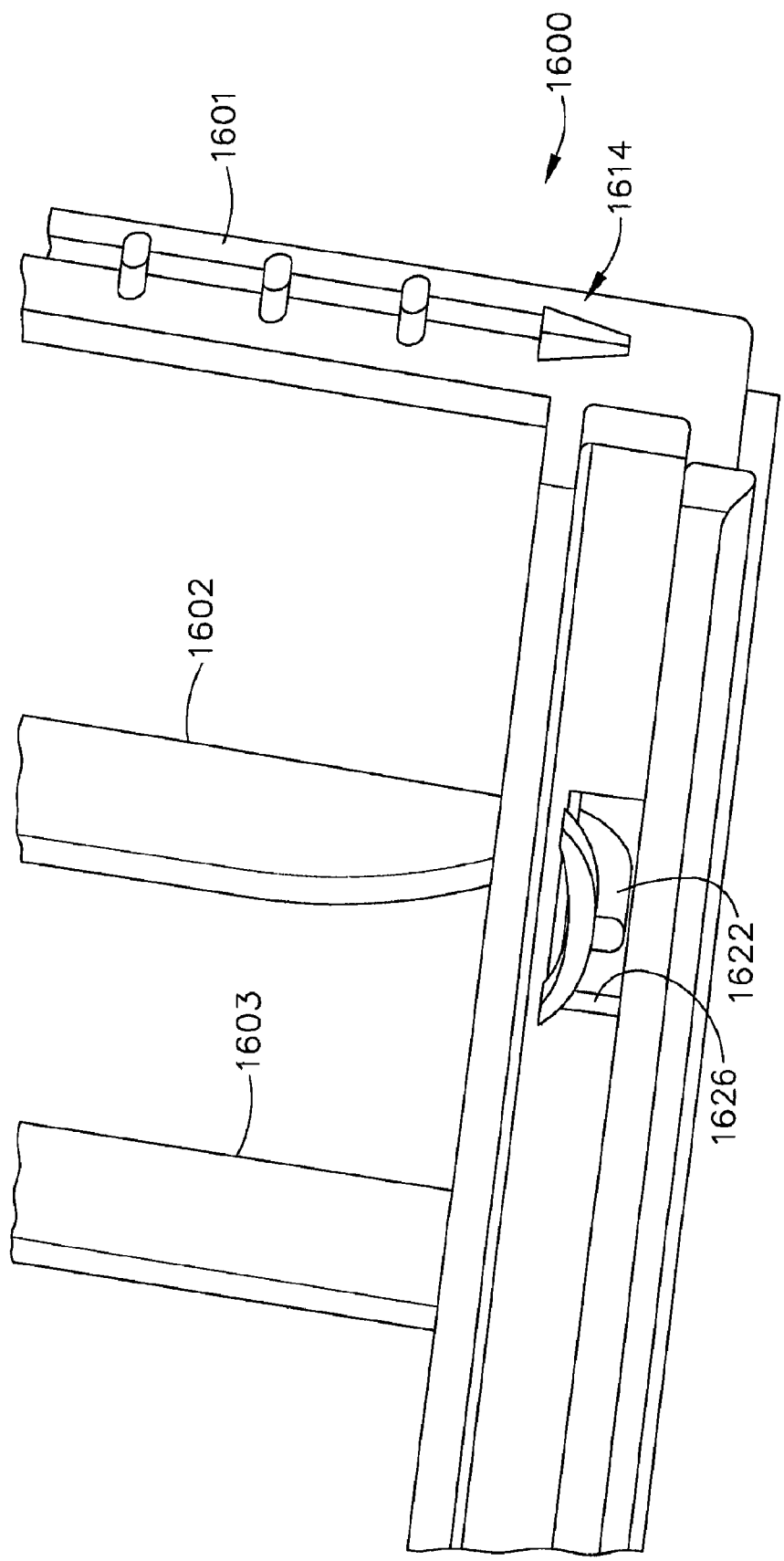
FIG. 47 is a back perspective view of a lower portion of the lateral fence of FIG. 43.

In FIG. 42, a lateral plate 1500 for a localization fixture includes molded horizontal grid members 1502. To enhance the ability to select insertion points that would ordinarily lie behind one of the grid members 1502, each grid member 1502 includes a left and right undulating portion 1504, 1506 on each side of a horizontal portion 1508. Thus, when using the sleeve or probe to move a particular grid member 1502 either up or down, these undulating portions 1504, 1506 horizontally extend to allow greater displacement of the horizontal portion 1508.

In FIGS. 43-47, an alternative lateral fence 1600 for a localization fixture includes vertical guide vanes 1602 that are advantageously detachable and laterally repositionable so as to not obscure possible insertion points. Further, each vertical guide vane 1602 includes a distally outwardly bowed shaped 1604 presenting upwardly ramped surface 1606 to a downwardly ramped lower bar 1608 and an upwardly ramped surface 1610 to a downwardly ramped upper bar 1612 of a lateral fence frame 1614, thus reacting distal pressure upon each vertical guide vane 1602 into the frame 1614 through a strong edge-on portion of the guide vane 1602. Left, center and right fixed vertical supports 1601, 1603, 1605 provide rigidity to the frame 1614. A top pin 1616 projects horizontally and distally away from a top end of each guide vane 1602. An upwardly curved cross bar 1618 is attached at its aft midpoint on top of the top pin 1616. Similarly, a bottom pin 1620 projects horizontally and distally away from a bottom end of each guide vane 1602. An upwardly curved cross bar 1622 is attached at its aft midpoint on top of the bottom pin 1620. A series of horizontal and rectangular slots 1624 are spaced along the upper bar 1612 and a series of horizontal and rectangular slots 1626 are spaced along the lower bar 1608. A pair of vertically aligned slots 1624, 1626 receive the respective curved cross bars 1618, 1622 of a guide vane 1602. Each cross bar 1618, 1622 is resiliently deformed into a more straight configuration during insertion and thereafter resists withdrawal. Each slot 1624, 1626 is sufficiently elongate to allow some lateral adjustment even without detachment.

Figure 48:
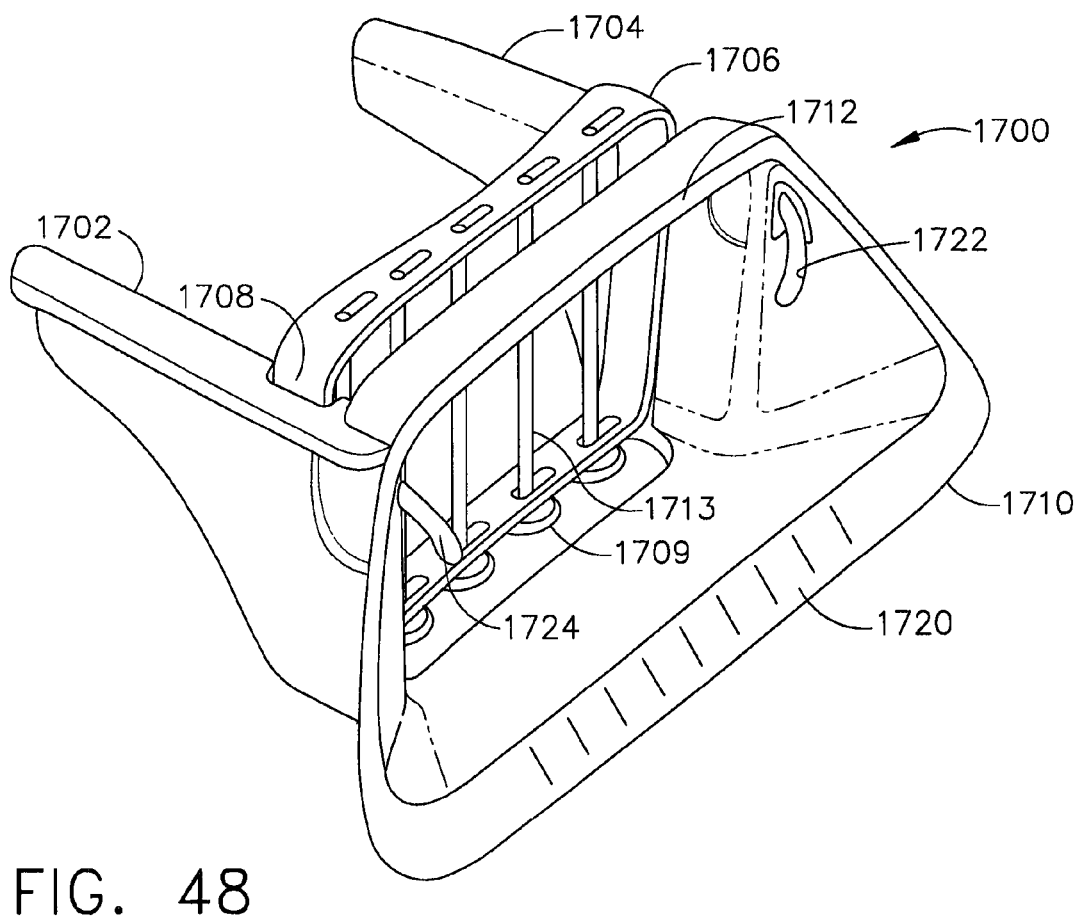
FIG. 48 is a top left perspective view of an alternative box localization fixture for the MRI biopsy system of FIG. 1.
Figure 49:
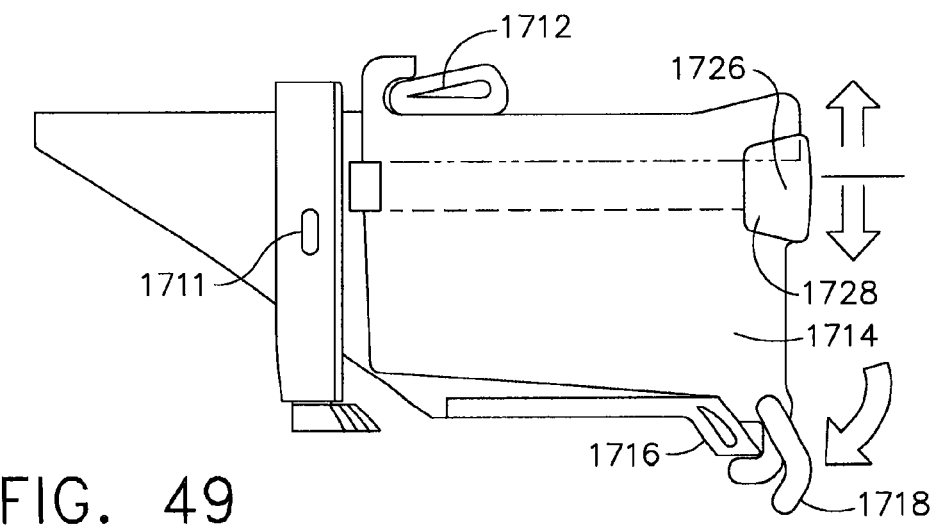
FIG. 49 is a left view in elevation of the alternative box localization fixture of FIG. 48 with an X-axis guide plate adjustably locked therein, which in turn supports a locked Y-axis guide frame.

In FIGS. 48-49, an alternative box localization fixture 1700 for the MRI biopsy system of FIG. 1 includes left and right flanges 1702, 1704 shaped for insertion into a breast coil (not shown). Bridged at the base of the flanges 1702, 1704, a lateral fence 1706 is downwardly inserted into frame channels 1708 for compressing the lateral side of a patient's breast, top and bottom. The lateral fence 1706 is slightly curved on top and the corners are more "human". Adjustment knobs 1709 on the bottom of each vertical guide rod 1713 in the lateral frame 1708 allow for lateral adjustment to reach otherwise obscured locations. The lateral fence 1706 advantageously pivots by twisting PC around a center point 1711 (FIG. 49) for compliance with the breast. The flanges 1702, 1704 are integral to a carrier frame 1710 that includes an upper bar 1712 spaced away from the lateral fence 1706 and having a top edge that opens up for increased visibility. In FIG. 49, an X-plate guide 1714 is vertically oriented resting upon a lower surface 1716 of the carrier frame 1710 with a tablesaw-type lock 1718 about its proximal edge. A lateral measurement scale 1720 (FIG. 48) assists in lateral position. Further support to the X-plate guide 1714 is received from a proximally open hook on a top, distal corner of the X-plate guide 1714 that hooks onto the upper bar 1712. It should be appreciated that the front edge of the carrier frame 1710 is gas assist with side pockets of gas on L-legs that attach to the breast coil, providing strength and accurate hanging of the system from the breast coil. Right and left locking cams 1722, 1724 lock the entire carrier frame 1710 into the upper bar 1712 to remove any tolerance build-up. A Y-height fence 1726 grips the parallel proximal and distal vertical edges of the X-plate guide 1714 for vertical height adjustment, with a proximal tablesaw-type lock 1728.

In FIGS. 50-53, an alternative fiducial holder 1800 for the localization fixture of FIG. 1 is depicted. A threaded hub 1802 receives a fiducial as depicted in FIG. 4 or as described below. A proximal channel arm 1804 engages a primary targeting rail with a distal locking channel 1806 that grips the primary targeting rail until a pair of release arms 1808, 1810 spread the distal locking channel 1806.

Figure 54:
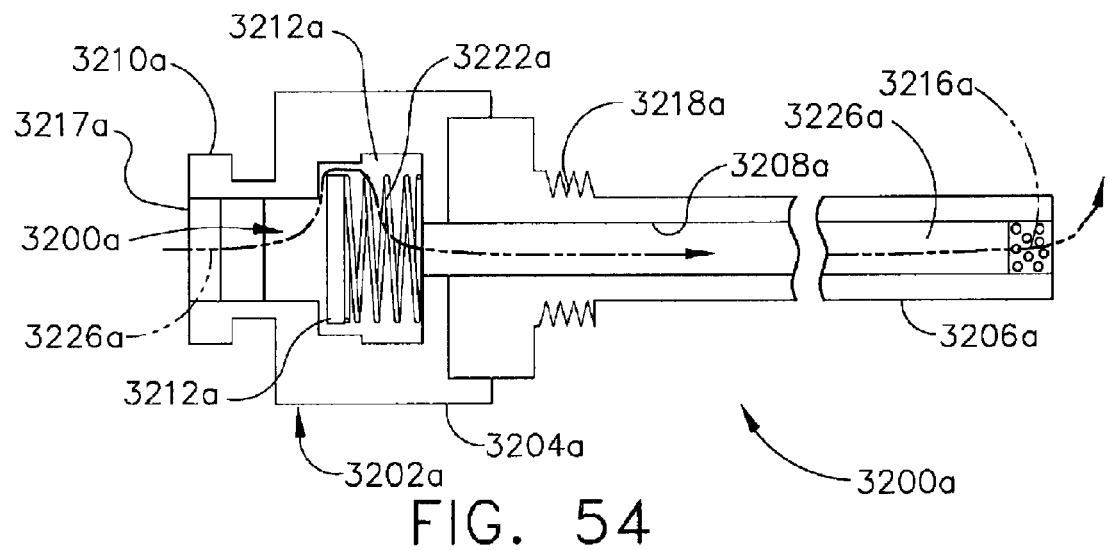
FIG. 54 is a top diagrammatic view of a disposable fiducial for the fiducial holder of FIG. 51.

In FIG. 54, a short fiducial instrument 3200a is an example of the fudicial 262 in FIG. 4 used with a localization fixture to locate a coordinate at an external point on the patient's skin. A clear polycarbonate body 3202a is assembled from a valve body 3204a attached to a hollow snout 3206a. An imaging lumen 3208a passes longitudinally from a proximal fill spout 3210a proximally extending from the valve body 3204a, through a one-way valve chamber 3212a into an elongate cavity 3214a in the hollow snout 3206a whose distal end is partially sealed by a porous plug 3216a. Examples of materials for the porous plug 3216a include porous PTFE, porous polyethylene, porous polypropoylene, polystyrene, and glass frit. External threads 3218a on a proximal end of the hollow snout 3206a allow for engagement to a holder, such as monocle or sleeve mount. In use, imagable fluid, such as but not limited to those materials described herein, are inserted into the proximal fill spout 3210a by inserting a syringe needle (not shown) through a septum 3217a that seals the proximal fill spout 3210a, causing a seal 3220a to unseat in the valve chamber 3212a compressing valve spring 3222a as the fluid enters the elongate chamber 3214a as depicted by arrow 3224a while air evacuates through porous plug 3216a as depicted by arrow 3226a. The end user continues to fill until evidently filled, as viewed through a clear polycarbonate body 3202a, when resistance is felt to forcing in more fluid, when the fill spout 3210a appears full, or when fluid begins to ooze through the porous plug 3216a. It should be appreciated that a two-way valve may be included that would allow an over-pressure to release fluid or for a user to withdraw fluid. In addition, the septum 3217a may suffice to hold fluid in the short fiducial instrument 3200a.

Figure 55:
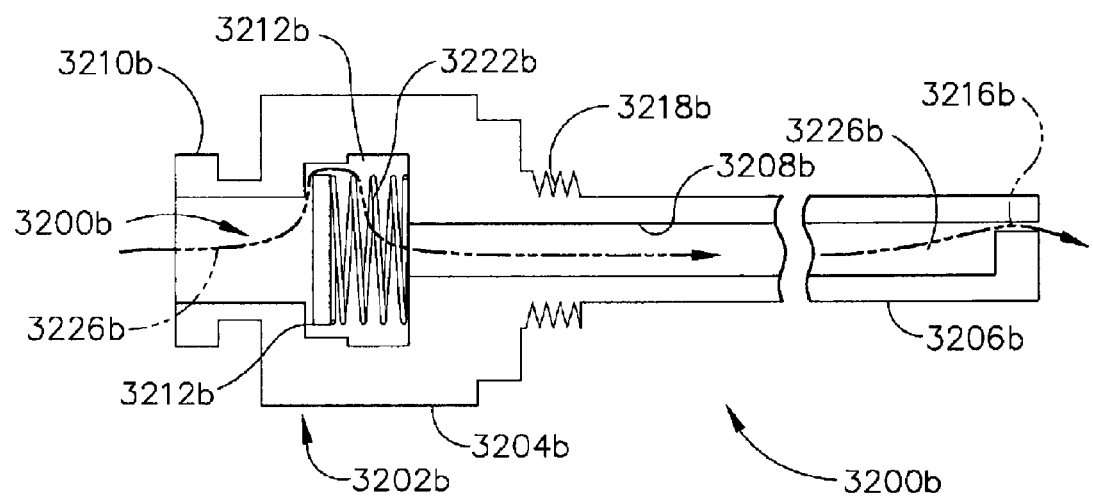
FIG. 55 is a top diagrammatic view of an alternate disposable fiducial for the fiducial holder of FIG. 51.

In FIG. 55, a long fiducial instrument 3200b is an example of an imaging obturator or stylet or alternate features for a fiducial used external to the patient. Although not shown in FIG. 55 for clarity, a second open lumen may be included for inserting a tool. A piercing tip may also be included for use as an introducer obturator with an open ended sleeve. A clear polycarbonate body 3202b has an integral valve body portion 3204b formed with a hollow snout portion 3206b. An imaging lumen 3208b passes longitudinally from a proximal pipe fitting 3210b proximally extending from the valve body portion 3204b, through a one-way valve chamber 3212b into an elongate cavity 3214b in the hollow snout 3206b whose distal end is partially sealed by a small vent hole 3216b. External threads 3218b on a proximal end of the hollow snout 3206b allow for engagement to a holder, such as a sleeve hub.

In use, imagable fluid, such as but not limited to those materials described herein, are inserted into the proximal pipe fitting 3210b, causing a seal 3220b to unseat in the valve chamber 3212b compressing closure valve spring 3222b as the fluid enters the elongate chamber 3214b as depicted by arrow 3224b while air evacuates through vent hole 3216b as depicted by arrow 3226b. After filling, surface tension of the liquid prevents loss of fluid through the vent hole 3216b.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. For example, other imaging modalities may benefit from aspects of the present invention. As another example, a fiduciary marker separate from the lateral plate may be positioned to a specific point on the exterior of the patient's breast as part of a guidance assembly.

What is claimed is:

1. An apparatus for performing a minimally invasive medical procedure with reference to a diagnostic image taken of a patient's breast, the apparatus comprising:
a medial compression member;
a lateral compression member movable relative to the medial compression member to compress the patient's breast; and
a biopsy probe support positionable relative to the lateral compression member, wherein the biopsy probe support further comprises a monocle positionable proximate to the patient's breast operatively configured to guide marking and scoring of an insertion point, wherein the monocle includes a reticule positionable in a first position along an axis of penetration, wherein the monocle is operable to rotate the reticule to a second position not along the axis of penetration after marking and scoring the insertion point.

2. The apparatus of claim 1, further comprising:
a medial plate supporting the medial compression member; and
a lateral plate supporting the lateral compression member, wherein the medial plate is operable to translate in opposition to the lateral plate;
wherein the medial plate includes a proximally extending handle, the lateral plate including a handle extending proximate to the medial plate handle, wherein moving the handles in unison centers the medial and lateral compression members upon a patient's breast, and squeezing the two handles together effects compression of the patient's breast.

3. The apparatus of claim 1, further comprising:
a medial plate supporting the medial compression member;
a lateral plate supporting the lateral compression member;
a base plate including a lateral guide surface, wherein the lateral plate is operable to translate in the lateral guide surface of the base plate;
a medial guide surface defined in a selected one of the base plate and the lateral plate;
a lateral plate locking member coupled between the base and lateral plates; and
a medial plate locking member coupled between the medial plate and the medial guide surface;
wherein the medial guide surface is defined in the base plate distal to the lateral plate guide surface, the lateral plate locking member comprising a cam lock locking the lateral plate to the base plate and the medial plate locking member comprising a sliding attachment between the medial and lateral plates movable to effect locking binding therebetween.

4. The apparatus of claim 1, wherein the biopsy probe support further comprises a cradle positioned to support a proximal lower portion of a biopsy device.

5. The apparatus of claim 1, further comprising a proximally biased guard to mitigate inadvertent contact with the biopsy probe support.

6. The apparatus of claim 5, wherein the proximally biased guard comprises a gas charged cylinder extending a guard rail proximally.

7. The apparatus of claim 6, wherein the proximally biased guard comprises a pivotally attached arm and a spring positioned to rotate the arm from a lateral to a proximal direction.

8. The apparatus of claim 1, further comprising an upper and lower horizontal frame and a guide surface extending distal to the lower horizontal frame, the biopsy probe support comprising a vertically aligned plate sized to laterally slide between the upper and lower frames.

9. The apparatus of claim 8, further comprising a lock attached to the plate operatively configured to latch to a selected one of the upper and the lower horizontal frames.

10. The apparatus of claim 8, further comprising a vertical support slidingly gripping proximal and distal edges of the plate and including a lock operatively configured to lock the vertical support to the plate.

11. The apparatus of claim 1, wherein the lateral compression member comprises a lateral fence having a plurality of detachable rails.

12. The apparatus of claim 11, wherein a lateral fence includes opposing and parallel frame rails including spaced attachment openings for the plurality of detachable rails, each opening sized to allow repositioning of the detachable rails within the engaged opening.

13. The apparatus of claim 1, wherein the monocle is operatively configured to engage a fiducial, the fiducial comprising:
a housing formed of a magnetic resonance imaging (MRI) compatible material defining an internal cavity;
a port formed in the housing communicating with the internal cavity and operatively configured to receive MRI imagable material by an end user; and
a vent formed in the housing for allowing air evacuation during filling.

14. The apparatus of claim 13
wherein the housing includes an elongate portion and a proximal portion, wherein the proximal portion includes an external threaded portion, wherein the external threaded portion is operable to engage the monocle.

15. The apparatus of claim 13, wherein the port comprises a septum.

16. The apparatus of claim 13, wherein the port comprises a one-way valve.

17. The apparatus of claim 13, wherein the port comprises a leur fitting.

18. The apparatus of claim 13, wherein the housing comprises clear polycarbonate.

19. The apparatus of claim 13, wherein the vent comprises a porous plug.

20. The apparatus of claim 19, wherein the porous plug is formed from a material selected from a group consisting of porous PTFE, porous polyethylene, porous polypropylene, porous polystyrene, and glass frit.

21. The apparatus of claim 1, further comprising:
a base member; and
a removable tray adjustably locked to the base member, wherein the tray comprises a lateral opening;
wherein the biopsy probe support further comprises a pedestal and a z-axis track associated with the pedestal, wherein the pedestal is positionable within the lateral opening of the removable tray, wherein the z-axis track is positionable along the pedestal, wherein a desired insertion point relative to the lateral compression member may be remotely set on the biopsy probe support prior to locking the removable tray to the base member, wherein the monocle is positionable along the z-axis track.

22. The apparatus of claim 21, wherein the biopsy probe support comprises a lateral adjustment, a height adjustment, and a depth of penetration stop adjustment.

23. The apparatus of claim 1 further comprising:
a pedestal member positionably coupled to the lateral compression member for locating a lateral coordinate; and
a targeting rail positionably coupled to the pedestal for locating a vertical coordinate and including a biopsy guide defining an axis of penetration;
wherein the biopsy probe support is positionably coupled to the targeting rail, wherein the biopsy probe support and the targeting rail are laterally and vertically orthogonally offset from the axis of penetration.

24. The apparatus of claim 23, wherein the targeting rail is rotatably coupled to the pedestal member to define a selectable penetration angle.

25. The apparatus of claim 23, wherein the targeting rail includes attachment fixtures on each lateral side and wherein the targeting rail is operatively configured for attachment to both sides of the pedestal to increase access through the lateral compression member.

26. The apparatus of claim 23, further comprising a lateral scale proximate to the pedestal for reading a lateral coordinate.

27. The apparatus of claim 23, wherein the pedestal further comprises a height measurement scale affixed proximate to the targeting rail for reading a height coordinate.

28. The apparatus of claim 23, wherein the biopsy guide further comprises a home position reference, the apparatus further comprising a fiducial holder attachable to the biopsy guide at the home position reference and laterally sized to align a fiducial proximate to the patient's breast at an insertion point along an axis of penetration of the biopsy instrument.

29. The apparatus of claim 28, wherein the fiducial holder further comprises an integral fiducial comprising a magnetic resonance imaging (MRI) imagable material.

30. The apparatus of claim 28, wherein the fiducial holder further comprises a polymer spring operatively configured to engage the biopsy guide.

31. The apparatus of claim 28, wherein the fiducial holder further comprises an engagement member operatively configured to slidingly engage the biopsy guide to the home position reference.

32. The apparatus of claim 1, wherein the biopsy probe support further comprises a z-axis rail having a proximal end and a distal end, where the monocle is pivotally attached to the distal end of the z-axis rail, wherein the monocle is remotely pivoted by an actuating member on the proximal end of the z-axis rail.

* * * * *